(12) United States Patent
Shelton, IV et al.

(10) Patent No.: US 8,215,531 B2
(45) Date of Patent: *Jul. 10, 2012

(54) SURGICAL STAPLING INSTRUMENT HAVING A MEDICAL SUBSTANCE DISPENSER

(75) Inventors: Frederick E. Shelton, IV, Hillsboro, OH (US); Joseph C. Hueil, Loveland, OH (US); Jerome R. Morgan, Cincinnati, OH (US); Leslie M. Fugikawa, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/696,397

(22) Filed: Jan. 29, 2010

(65) Prior Publication Data

US 2010/0181364 A1    Jul. 22, 2010

Related U.S. Application Data

(63) Continuation-in-part of application No. 11/731,521, filed on Mar. 30, 2007, now abandoned, which is a continuation of application No. 11/271,234, filed on Nov. 10, 2005, now Pat. No. 7,354,447, which is a continuation-in-part of application No. 11/141,753, filed on Jun. 1, 2005.

(60) Provisional application No. 60/591,694, filed on Jul. 28, 2004.

(51) Int. Cl.
*A61B 17/068* (2006.01)

(52) U.S. Cl. .................... 227/180.1; 227/175.1; 227/19; 606/219; 606/167

(58) Field of Classification Search ............... 227/175.1, 227/180.1, 19; 606/219, 167
See application file for complete search history.

(56) References Cited

U.S. PATENT DOCUMENTS

| | | |
|---|---|---|
| 3,490,675 A | 1/1970 | Green et al. |
| 3,643,851 A | 2/1972 | Green et al. |
| 3,662,939 A | 5/1972 | Bryan |
| 3,717,294 A | 2/1973 | Green |
| 3,819,100 A | 6/1974 | Noiles et al. |
| RE28,932 E | 8/1976 | Noiles et al. |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,415,112 A | 11/1983 | Green |

(Continued)

FOREIGN PATENT DOCUMENTS

CA       2458946 A1    3/2003

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Brian D Nash
*Assistant Examiner* — Michelle Lopez

(57) ABSTRACT

In various embodiments, an assembly of a surgical instrument is disclosed. The assembly includes a housing, a cutting member relatively movable with respect to the housing, and an agent cartridge connected to the housing. The agent cartridge houses a medical agent. The assembly is configured to deliver the medical agent proximate a cutting surface of the cutting member.

15 Claims, 19 Drawing Sheets

U.S. PATENT DOCUMENTS

| | | | |
|---|---|---|---|
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,610,383 A | 9/1986 | Rothfuss et al. |
| 4,629,107 A | 12/1986 | Fedotov et al. |
| 4,632,290 A | 12/1986 | Green et al. |
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,844,068 A | 7/1989 | Arata et al. |
| 4,869,414 A | 9/1989 | Green et al. |
| 4,869,415 A | 9/1989 | Fox |
| 4,941,623 A | 7/1990 | Pruitt |
| 4,944,443 A | 7/1990 | Oddsen et al. |
| 4,986,808 A | 1/1991 | Broadwin et al. |
| 4,988,334 A | 1/1991 | Hornlein et al. |
| 5,015,227 A | 5/1991 | Broadwin et al. |
| 5,024,652 A | 6/1991 | Dumenek et al. |
| 5,065,929 A | 11/1991 | Schulze et al. |
| 5,071,430 A | 12/1991 | de Salis et al. |
| 5,129,570 A | 7/1992 | Schulze et al. |
| 5,137,198 A | 8/1992 | Nobis et al. |
| 5,139,513 A | 8/1992 | Segato |
| 5,156,614 A | 10/1992 | Green et al. |
| 5,158,567 A | 10/1992 | Green |
| 5,188,102 A | 2/1993 | Idemoto et al. |
| 5,190,517 A | 3/1993 | Zieve et al. |
| 5,207,697 A | 5/1993 | Carusillo et al. |
| 5,221,036 A | 6/1993 | Takase |
| 5,222,975 A | 6/1993 | Crainich |
| 5,236,440 A | 8/1993 | Hlavacek |
| 5,258,009 A | 11/1993 | Conners |
| 5,282,829 A | 2/1994 | Hermes |
| 5,304,204 A | 4/1994 | Bregen |
| 5,312,329 A | 5/1994 | Beaty et al. |
| 5,330,502 A | 7/1994 | Hassler et al. |
| 5,342,395 A | 8/1994 | Jarrett et al. |
| 5,342,396 A | 8/1994 | Cook |
| 5,350,400 A | 9/1994 | Esposito et al. |
| 5,352,238 A | 10/1994 | Green et al. |
| 5,358,510 A | 10/1994 | Luscombe et al. |
| 5,366,479 A | 11/1994 | McGarry et al. |
| 5,391,180 A | 2/1995 | Tovey et al. |
| 5,395,312 A | 3/1995 | Desai |
| 5,405,072 A | 4/1995 | Zlock et al. |
| 5,413,272 A | 5/1995 | Green et al. |
| 5,425,745 A | 6/1995 | Green et al. |
| 5,465,895 A | 11/1995 | Knodel et al. |
| 5,476,479 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,484,398 A | 1/1996 | Stoddard |
| 5,487,499 A | 1/1996 | Sorrentino et al. |
| 5,497,933 A | 3/1996 | DeFonzo et al. |
| 5,505,363 A | 4/1996 | Green et al. |
| 5,529,235 A | 6/1996 | Boiarski et al. |
| 5,535,934 A | 7/1996 | Boiarski et al. |
| 5,549,628 A | 8/1996 | Cooper et al. |
| 5,554,169 A | 9/1996 | Green et al. |
| 5,556,416 A | 9/1996 | Clark et al. |
| 5,562,241 A | 10/1996 | Knodel et al. |
| 5,564,615 A | 10/1996 | Bishop et al. |
| 5,577,654 A | 11/1996 | Bishop |
| 5,588,579 A | 12/1996 | Schnut et al. |
| 5,601,224 A | 2/1997 | Bishop et al. |
| 5,607,094 A | 3/1997 | Clark et al. |
| 5,618,303 A | 4/1997 | Marlow et al. |
| 5,628,446 A | 5/1997 | Geiste et al. |
| 5,630,539 A | 5/1997 | Plyley et al. |
| 5,639,008 A | 6/1997 | Gallagher et al. |
| 5,651,491 A | 7/1997 | Heaton et al. |
| 5,653,373 A | 8/1997 | Green et al. |
| 5,662,258 A | 9/1997 | Knodel et al. |
| 5,667,527 A | 9/1997 | Cook |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,692,668 A | 12/1997 | Schulze et al. |
| 5,704,534 A | 1/1998 | Huitema et al. |
| 5,711,472 A | 1/1998 | Bryan |
| 5,715,987 A | 2/1998 | Kelley et al. |
| 5,725,554 A | 3/1998 | Simon et al. |
| 5,730,758 A | 3/1998 | Allgeyer |
| 5,732,871 A | 3/1998 | Clark et al. |
| 5,749,893 A | 5/1998 | Vidal et al. |
| 5,752,644 A | 5/1998 | Bolanos et al. |
| 5,758,814 A | 6/1998 | Gallagher et al. |
| 5,762,256 A | 6/1998 | Mastri et al. |
| 5,779,130 A | 7/1998 | Alesi et al. |
| 5,782,396 A | 7/1998 | Mastri et al. |
| 5,782,859 A | 7/1998 | Nicholas et al. |
| 5,797,536 A | 8/1998 | Smith et al. |
| 5,836,503 A | 11/1998 | Ehrenfels et al. |
| 5,839,639 A | 11/1998 | Sauer et al. |
| 5,911,353 A | 6/1999 | Bolanos et al. |
| 5,931,847 A | 8/1999 | Bittner et al. |
| 5,941,442 A | 8/1999 | Geiste et al. |
| 5,954,259 A | 9/1999 | Viola et al. |
| 6,083,242 A | 7/2000 | Cook |
| 6,099,551 A | 8/2000 | Gabbay |
| 6,102,271 A | 8/2000 | Longo et al. |
| 6,109,500 A | 8/2000 | Alli et al. |
| 6,126,058 A | 10/2000 | Adams et al. |
| 6,171,330 B1 | 1/2001 | Benchetrit |
| 6,193,129 B1 | 2/2001 | Bittner et al. |
| 6,214,028 B1 | 4/2001 | Yoon et al. |
| 6,228,084 B1 | 5/2001 | Kirwan, Jr. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,309,403 B1 | 10/2001 | Minor et al. |
| 6,315,184 B1 | 11/2001 | Whitman |
| 6,358,224 B1 | 3/2002 | Tims et al. |
| 6,387,113 B1 | 5/2002 | Hawkins et al. |
| 6,387,114 B2 | 5/2002 | Adams |
| RE37,814 E | 8/2002 | Allgeyer |
| 6,443,973 B1 | 9/2002 | Whitman |
| 6,488,196 B1 | 12/2002 | Fenton, Jr. |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,601,749 B2 | 8/2003 | Sullivan et al. |
| 6,616,686 B2 | 9/2003 | Coleman et al. |
| 6,629,630 B2 | 10/2003 | Adams |
| 6,629,988 B2 | 10/2003 | Weadock |
| 6,667,825 B2 | 12/2003 | Lu et al. |
| 6,681,979 B2 | 1/2004 | Whitman |
| 6,695,199 B2 | 2/2004 | Whitman |
| 6,698,643 B2 | 3/2004 | Whitman |
| 6,716,232 B1 | 4/2004 | Vidal et al. |
| 6,716,233 B1 | 4/2004 | Whitman |
| 6,755,338 B2 | 6/2004 | Hahnen et al. |
| 6,805,273 B2 | 10/2004 | Bilotti et al. |
| 6,830,174 B2 | 12/2004 | Hillstead et al. |
| RE38,708 E | 3/2005 | Bolanos et al. |
| 6,874,669 B2 | 4/2005 | Adams et al. |

| Patent No. | Date | Inventor |
|---|---|---|
| 6,945,444 B2 | 9/2005 | Gresham et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,922 B2 | 12/2005 | Bilotti et al. |
| 7,018,390 B2 | 3/2006 | Turovskiy et al. |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,056,330 B2 | 6/2006 | Gayton |
| 7,077,856 B2 | 7/2006 | Whitman |
| 7,108,709 B2 | 9/2006 | Cummins |
| 7,112,214 B2 | 9/2006 | Peterson et al. |
| 7,114,642 B2 | 10/2006 | Whitman |
| 7,140,527 B2 | 11/2006 | Ehrenfels et al. |
| 7,141,055 B2 | 11/2006 | Abrams et al. |
| 7,147,138 B2 | 12/2006 | Shelton, IV |
| 7,147,648 B2 | 12/2006 | Lin |
| 7,147,650 B2 | 12/2006 | Lee |
| 7,156,863 B2 | 1/2007 | Sonnenschein et al. |
| 7,159,750 B2 | 1/2007 | Racenet et al. |
| 7,182,239 B1 | 2/2007 | Myers |
| 7,188,758 B2 | 3/2007 | Viola et al. |
| 7,208,005 B2 | 4/2007 | Frecker et al. |
| 7,210,609 B2 | 5/2007 | Leiboff et |
| 7,213,736 B2 | 5/2007 | Wales et al. |
| 7,220,272 B2 | 5/2007 | Weadock |
| 7,235,089 B1 | 6/2007 | McGuckin, Jr. |
| 7,237,708 B1 | 7/2007 | Guy et al. |
| 7,246,734 B2 | 7/2007 | Shelton, IV |
| 7,278,563 B1 | 10/2007 | Green |
| 7,300,450 B2 | 11/2007 | Vleugels et al. |
| 7,303,106 B2 | 12/2007 | Milliman et al. |
| 7,303,108 B2 | 12/2007 | Shelton, IV |
| 7,328,828 B2 | 2/2008 | Ortiz et al. |
| 7,334,717 B2 | 2/2008 | Rethy et al. |
| 7,338,513 B2 | 3/2008 | Lee et al. |
| 7,343,920 B2 | 3/2008 | Toby et al. |
| 7,354,447 B2 * | 4/2008 | Shelton et al. ............... 606/219 |
| 7,364,060 B2 | 4/2008 | Milliman |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,481,347 B2 | 1/2009 | Roy |
| 7,481,824 B2 | 1/2009 | Boudreaux et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 7,549,564 B2 | 6/2009 | Boudreaux |
| 7,559,450 B2 | 7/2009 | Wales et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,624,902 B2 | 12/2009 | Marczyk et al. |
| 7,631,793 B2 | 12/2009 | Rethy et al. |
| 7,644,848 B2 | 1/2010 | Swayze et al. |
| 7,651,498 B2 | 1/2010 | Shifrin et al. |
| 7,658,311 B2 | 2/2010 | Boudreaux |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,686,826 B2 | 3/2010 | Lee et al. |
| 7,699,204 B2 * | 4/2010 | Viola ........................ 227/175.1 |
| 7,717,312 B2 | 5/2010 | Beetel |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,726,537 B2 | 6/2010 | Olson et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,780,054 B2 | 8/2010 | Wales |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,080 B2 | 11/2010 | Schwemberger |
| 7,845,533 B2 | 12/2010 | Marczyk et al. |
| 7,845,537 B2 | 12/2010 | Shelton, IV et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,909,221 B2 | 3/2011 | Viola et al. |
| 7,950,560 B2 | 5/2011 | Zemlok et al. |
| 8,002,795 B2 | 8/2011 | Beetel |
| D650,074 S | 12/2011 | Hunt et al. |
| 2003/0065358 A1 * | 4/2003 | Frecker et al. ............... 606/205 |
| 2003/0105478 A1 | 6/2003 | Whitman et al. |
| 2003/0130677 A1 | 7/2003 | Whitman et al. |
| 2004/0006372 A1 | 1/2004 | Racenet et al. |
| 2004/0094597 A1 | 5/2004 | Whitman et al. |
| 2004/0167572 A1 | 8/2004 | Roth et al. |
| 2004/0222268 A1 | 11/2004 | Bilotti et al. |
| 2004/0243176 A1 | 12/2004 | Hahnen et al. |
| 2004/0254608 A1 | 12/2004 | Huitema et al. |
| 2004/0267310 A1 | 12/2004 | Racenet et al. |
| 2005/0059997 A1 | 3/2005 | Bauman et al. |
| 2005/0080454 A1 | 4/2005 | Drews et al. |
| 2005/0103819 A1 | 5/2005 | Racenet et al. |
| 2005/0107824 A1 | 5/2005 | Hillstead et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |

| Pub. No. | Date | Inventor |
|---|---|---|
| 2005/0145675 A1 | 7/2005 | Hartwick et al. |
| 2005/0165435 A1 | 7/2005 | Johnston et al. |
| 2005/0184121 A1 | 8/2005 | Heinrich |
| 2005/0187572 A1 | 8/2005 | Johnston et al. |
| 2005/0187576 A1 | 8/2005 | Whitman et al. |
| 2005/0192609 A1 | 9/2005 | Whitman et al. |
| 2005/0192628 A1 | 9/2005 | Viola |
| 2005/0216055 A1 | 9/2005 | Scirica et al. |
| 2005/0230453 A1* | 10/2005 | Viola ..................... 227/176.1 |
| 2005/0240222 A1 | 10/2005 | Shipp |
| 2005/0274768 A1 | 12/2005 | Cummins et al. |
| 2006/0011699 A1 | 1/2006 | Olson et al. |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0085033 A1 | 4/2006 | Criscuolo et al. |
| 2006/0190031 A1 | 8/2006 | Wales et al. |
| 2006/0212069 A1 | 9/2006 | Shelton, IV |
| 2006/0226196 A1 | 10/2006 | Hueil et al. |
| 2006/0229665 A1 | 10/2006 | Wales et al. |
| 2006/0235469 A1 | 10/2006 | Viola |
| 2006/0241692 A1 | 10/2006 | McGuckin, Jr. et al. |
| 2006/0259073 A1 | 11/2006 | Miyamoto et al. |
| 2006/0271102 A1 | 11/2006 | Bosshard et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0027469 A1 | 2/2007 | Smith et al. |
| 2007/0073341 A1 | 3/2007 | Smith |
| 2007/0078484 A1 | 4/2007 | Talarico et al. |
| 2007/0102472 A1 | 5/2007 | Shelton, IV |
| 2007/0106317 A1 | 5/2007 | Shelton, IV et al. |
| 2007/0114261 A1 | 5/2007 | Ortiz et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0197954 A1 | 8/2007 | Keenan |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0246505 A1 | 10/2007 | Pace-Floridia et al. |
| 2007/0260278 A1 | 11/2007 | Wheeler et al. |
| 2007/0295780 A1 | 12/2007 | Shelton et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082125 A1 | 4/2008 | Murray et al. |
| 2008/0082126 A1 | 4/2008 | Murray et al. |
| 2008/0140115 A1 | 6/2008 | Stopek |
| 2008/0167522 A1 | 7/2008 | Giordano et al. |
| 2008/0167644 A1 | 7/2008 | Shelton et al. |
| 2008/0167671 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0296346 A1 | 12/2008 | Shelton, IV et al. |
| 2008/0300580 A1 | 12/2008 | Shelton, IV et al. |
| 2008/0300613 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0314957 A1 | 12/2008 | Boudreaux |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 | 3/2009 | Smith et al. |
| 2009/0076534 A1 | 3/2009 | Shelton, IV et al. |
| 2009/0108048 A1 | 4/2009 | Zemlok et al. |
| 2009/0149871 A9 | 6/2009 | Kagan et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0209990 A1 | 8/2009 | Yates et al. |
| 2009/0242610 A1 | 10/2009 | Shelton, IV et al. |
| 2009/0255978 A1 | 10/2009 | Viola et al. |
| 2009/0289096 A1 | 11/2009 | Shelton, IV et al. |
| 2010/0001036 A1 | 1/2010 | Marczyk et al. |
| 2010/0012704 A1 | 1/2010 | Tarinelli Racenet et al. |
| 2010/0032470 A1 | 2/2010 | Hess et al. |
| 2010/0065605 A1 | 3/2010 | Shelton, IV et al. |
| 2010/0069942 A1 | 3/2010 | Shelton, IV |
| 2010/0072252 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0096435 A1 | 4/2010 | Fuchs et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2011/0006099 A1 | 1/2011 | Hall et al. |
| 2011/0006101 A1 | 1/2011 | Hall et al. |
| 2011/0006103 A1 | 1/2011 | Laurent et al. |

| Pub. No. | Date | Inventor |
|---|---|---|
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139852 A1 | 6/2011 | Zingman |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |
| 2011/0163147 A1 | 7/2011 | Laurent et al. |
| 2011/0174860 A1 | 7/2011 | Shelton, IV et al. |
| 2011/0174863 A1 | 7/2011 | Shelton, IV et al. |
| 2011/0192882 A1 | 8/2011 | Hess et al. |
| 2011/0226837 A1 | 9/2011 | Baxter, III et al. |
| 2011/0233258 A1 | 9/2011 | Boudreaux |
| 2011/0253766 A1 | 10/2011 | Baxter, III et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0290857 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |

FOREIGN PATENT DOCUMENTS

| | | |
|---|---|---|
| CA | 2512960 A1 | 1/2006 |
| CA | 2514274 A1 | 1/2006 |
| CN | 1868411 A | 11/2006 |
| CN | 1915180 A | 2/2007 |
| DE | 273689 C | 5/1914 |
| DE | 1775926 A | 1/1972 |
| DE | 3036217 A1 | 4/1982 |
| DE | 3210466 A1 | 9/1983 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0387980 B1 | 10/1985 |
| EP | 0033548 B1 | 5/1986 |
| EP | 0276104 A2 | 7/1988 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |

| | | | | | | | |
|---|---|---|---|---|---|---|---|
| EP | 1095627 | A1 | 5/2001 | EP | 1129665 | B1 | 11/2006 |
| EP | 1256318 | B1 | 5/2001 | EP | 1400206 | B1 | 11/2006 |
| EP | 0806914 | B1 | 9/2001 | EP | 1721568 | A1 | 11/2006 |
| EP | 0768840 | B1 | 12/2001 | EP | 1256317 | B1 | 12/2006 |
| EP | 0908152 | B1 | 1/2002 | EP | 1728473 | A1 | 12/2006 |
| EP | 0872213 | B1 | 5/2002 | EP | 1728475 | A2 | 12/2006 |
| EP | 0862386 | B1 | 6/2002 | EP | 1479346 | B1 | 1/2007 |
| EP | 0949886 | B1 | 9/2002 | EP | 1484024 | B1 | 1/2007 |
| EP | 1238634 | A2 | 9/2002 | EP | 1754445 | A2 | 2/2007 |
| EP | 0858295 | B1 | 12/2002 | EP | 1759812 | A1 | 3/2007 |
| EP | 0656188 | B1 | 1/2003 | EP | 1767163 | A1 | 3/2007 |
| EP | 1284120 | A1 | 2/2003 | EP | 1769756 | A1 | 4/2007 |
| EP | 1287788 | A1 | 3/2003 | EP | 1769758 | A1 | 4/2007 |
| EP | 0717966 | B1 | 4/2003 | EP | 1581128 | B1 | 5/2007 |
| EP | 0869742 | B1 | 5/2003 | EP | 1785097 | A2 | 5/2007 |
| EP | 0829235 | B1 | 6/2003 | EP | 1790293 | A2 | 5/2007 |
| EP | 0887046 | B1 | 7/2003 | EP | 1800610 | A1 | 6/2007 |
| EP | 0852480 | B1 | 8/2003 | EP | 1300117 | B1 | 8/2007 |
| EP | 0891154 | B1 | 9/2003 | EP | 1813199 | A1 | 8/2007 |
| EP | 0813843 | B1 | 10/2003 | EP | 1813201 | A1 | 8/2007 |
| EP | 0873089 | B1 | 10/2003 | EP | 1813203 | A2 | 8/2007 |
| EP | 0856326 | B1 | 11/2003 | EP | 1813207 | A1 | 8/2007 |
| EP | 1374788 | A1 | 1/2004 | EP | 1813209 | A1 | 8/2007 |
| EP | 0741996 | B1 | 2/2004 | EP | 1487359 | B1 | 10/2007 |
| EP | 0814712 | B1 | 2/2004 | EP | 1599146 | B1 | 10/2007 |
| EP | 1402837 | A1 | 3/2004 | EP | 1839596 | A1 | 10/2007 |
| EP | 0705570 | B1 | 4/2004 | EP | 1402821 | B1 | 12/2007 |
| EP | 0959784 | B1 | 4/2004 | EP | 1872727 | A1 | 1/2008 |
| EP | 1407719 | A2 | 4/2004 | EP | 1897502 | A1 | 3/2008 |
| EP | 1086713 | B1 | 5/2004 | EP | 1330201 | B1 | 6/2008 |
| EP | 0996378 | B1 | 6/2004 | EP | 1702568 | B1 | 7/2008 |
| EP | 1426012 | A1 | 6/2004 | EP | 1943957 | A2 | 7/2008 |
| EP | 0833593 | B2 | 7/2004 | EP | 1943976 | A2 | 7/2008 |
| EP | 1442694 | A1 | 8/2004 | EP | 1593337 | B1 | 8/2008 |
| EP | 0888749 | B1 | 9/2004 | EP | 1970014 | A1 | 9/2008 |
| EP | 0959786 | B1 | 9/2004 | EP | 1980213 | A2 | 10/2008 |
| EP | 1459695 | A1 | 9/2004 | EP | 1759645 | B1 | 11/2008 |
| EP | 1473819 | A1 | 11/2004 | EP | 1990014 | A2 | 11/2008 |
| EP | 1477119 | A1 | 11/2004 | EP | 1693008 | B1 | 12/2008 |
| EP | 1479345 | A1 | 11/2004 | EP | 1759640 | 61 | 12/2008 |
| EP | 1479347 | A1 | 11/2004 | EP | 2000102 | A2 | 12/2008 |
| EP | 1479348 | A1 | 11/2004 | EP | 1736104 | B1 | 3/2009 |
| EP | 0754437 | B2 | 12/2004 | EP | 1749486 | B1 | 3/2009 |
| EP | 1025807 | B1 | 12/2004 | EP | 1721576 | B1 | 4/2009 |
| EP | 1001710 | B1 | 1/2005 | EP | 1733686 | B1 | 4/2009 |
| EP | 1520521 | A1 | 4/2005 | EP | 2044890 | A1 | 4/2009 |
| EP | 1520523 | A1 | 4/2005 | EP | 1745748 | B1 | 8/2009 |
| EP | 1520525 | A1 | 4/2005 | EP | 2090256 | A2 | 8/2009 |
| EP | 1522264 | A1 | 4/2005 | EP | 1813208 | B1 | 11/2009 |
| EP | 1523942 | A2 | 4/2005 | EP | 1607050 | B1 | 12/2009 |
| EP | 1550408 | A1 | 7/2005 | EP | 1566150 | B1 | 4/2010 |
| EP | 1557129 | A1 | 7/2005 | EP | 1813206 | B1 | 4/2010 |
| EP | 1064883 | B1 | 8/2005 | EP | 1769754 | B1 | 6/2010 |
| EP | 1067876 | B1 | 8/2005 | EP | 1535565 | B1 | 10/2010 |
| EP | 0870473 | B1 | 9/2005 | EP | 1702570 | B1 | 10/2010 |
| EP | 1157666 | B1 | 9/2005 | EP | 1785098 | B1 | 10/2010 |
| EP | 0880338 | B1 | 10/2005 | EP | 1627605 | B1 | 12/2010 |
| EP | 1158917 | B1 | 11/2005 | EP | 1813205 | B1 | 6/2011 |
| EP | 1344498 | B1 | 11/2005 | EP | 1785102 | B1 | 1/2012 |
| EP | 1330989 | B1 | 12/2005 | FR | 999646 | A | 2/1952 |
| EP | 0771176 | B2 | 1/2006 | FR | 1112936 | A | 3/1956 |
| EP | 1621138 | A2 | 2/2006 | FR | 2765794 | | 1/1999 |
| EP | 1621139 | A2 | 2/2006 | GB | 939929 | A | 10/1963 |
| EP | 1621141 | A2 | 2/2006 | GB | 1210522 | A | 10/1970 |
| EP | 1621145 | A2 | 2/2006 | GB | 1217159 | A | 12/1970 |
| EP | 1621151 | A2 | 2/2006 | GB | 1339394 | A | 12/1973 |
| EP | 1034746 | B1 | 3/2006 | GB | 2109241 | A | 6/1983 |
| EP | 1632191 | A2 | 3/2006 | GB | 2272159 | A | 5/1994 |
| EP | 1065981 | B1 | 5/2006 | GB | 2284242 | A | 5/1995 |
| EP | 1082944 | B1 | 5/2006 | GB | 2336214 | A | 10/1999 |
| EP | 1652481 | A2 | 5/2006 | GB | 2425903 | A | 11/2006 |
| EP | 1382303 | B1 | 6/2006 | JP | 6007357 | A | 1/1994 |
| EP | 1253866 | B1 | 7/2006 | JP | 7051273 | A | 2/1995 |
| EP | 1032318 | B1 | 8/2006 | JP | 8033641 | A | 2/1996 |
| EP | 1045672 | B1 | 8/2006 | JP | 8229050 | A | 9/1996 |
| EP | 1617768 | B1 | 8/2006 | JP | 2000033071 | A | 2/2000 |
| EP | 1693015 | A2 | 8/2006 | JP | 2000171730 | A | 6/2000 |
| EP | 1400214 | B1 | 9/2006 | JP | 2000287987 | A | 10/2000 |
| EP | 1702567 | A2 | 9/2006 | JP | 2000325303 | A | 11/2000 |

| | | | | | | | |
|---|---|---|---|---|---|---|---|
| JP | 2001286477 | A | 10/2001 | WO | WO 97/15237 | A1 | 5/1997 |
| JP | 2002143078 | A | 5/2002 | WO | WO 97/24073 | A1 | 7/1997 |
| JP | 2002369820 | A | 12/2002 | WO | WO 97/24993 | A1 | 7/1997 |
| JP | 2005505322 | T | 2/2005 | WO | WO 97/30644 | A1 | 8/1997 |
| JP | 2005103293 | A | 4/2005 | WO | WO 97/34533 | A1 | 9/1997 |
| JP | 2005131163 | A | 5/2005 | WO | WO 97/37598 | A1 | 10/1997 |
| JP | 2005131164 | A | 5/2005 | WO | WO 97/39688 | A2 | 10/1997 |
| JP | 2005131173 | A | 5/2005 | WO | WO 98/17180 | A1 | 4/1998 |
| JP | 2005131211 | A | 5/2005 | WO | WO 98/27880 | A1 | 7/1998 |
| JP | 2005131212 | A | 5/2005 | WO | WO 98/30153 | A1 | 7/1998 |
| JP | 2005137423 | A | 6/2005 | WO | WO 98/47436 | A1 | 10/1998 |
| JP | 2005152416 | A | 6/2005 | WO | WO 99/03407 | A1 | 1/1999 |
| JP | 2005524474 | A | 8/2005 | WO | WO 99/03408 | A1 | 1/1999 |
| JP | 2006-281405 | A | 10/2006 | WO | WO 99/03409 | A1 | 1/1999 |
| RU | 2008830 | C1 | 3/1994 | WO | WO 99/12483 | A1 | 3/1999 |
| RU | 2187249 | C2 | 8/2002 | WO | WO 99/12487 | A1 | 3/1999 |
| RU | 2225170 | C2 | 3/2004 | WO | WO 99/12488 | A1 | 3/1999 |
| SU | 189517 | A | 1/1967 | WO | WO 99/15086 | A1 | 4/1999 |
| SU | 328636 | A | 9/1972 | WO | WO 99/15091 | A1 | 4/1999 |
| SU | 886900 | A1 | 12/1981 | WO | WO 99/23933 | A2 | 5/1999 |
| SU | 1009439 | A | 4/1983 | WO | WO 99/23959 | A1 | 5/1999 |
| SU | 1333319 | A2 | 8/1987 | WO | WO 99/25261 | A1 | 5/1999 |
| SU | 1377053 | A1 | 2/1988 | WO | WO 99/29244 | A1 | 6/1999 |
| SU | 1561964 | A1 | 5/1990 | WO | WO 99/34744 | A1 | 7/1999 |
| SU | 1722476 | A1 | 3/1992 | WO | WO 99/45849 | A1 | 9/1999 |
| WO | WO 91/15157 | A1 | 10/1991 | WO | WO 99/48430 | A1 | 9/1999 |
| WO | WO 92/20295 | A1 | 11/1992 | WO | WO 99/51158 | A1 | 10/1999 |
| WO | WO 92/21300 | A1 | 12/1992 | WO | WO 00/24322 | A1 | 5/2000 |
| WO | WO 93/08755 | A1 | 5/1993 | WO | WO 00/24330 | A1 | 5/2000 |
| WO | WO 93/13718 | A1 | 7/1993 | WO | WO 00/41638 | A1 | 7/2000 |
| WO | WO 93/14690 | A1 | 8/1993 | WO | WO 00/48506 | A1 | 8/2000 |
| WO | WO 93/15648 | A1 | 8/1993 | WO | WO 00/53112 | A2 | 9/2000 |
| WO | WO 93/15850 | A1 | 8/1993 | WO | WO 00/54653 | A1 | 9/2000 |
| WO | WO 93/19681 | A1 | 10/1993 | WO | WO 00/57796 | A1 | 10/2000 |
| WO | WO 94/00060 | A1 | 1/1994 | WO | WO 00/64365 | A1 | 11/2000 |
| WO | WO 94/11057 | A1 | 5/1994 | WO | WO 00/72762 | A1 | 12/2000 |
| WO | WO 94/12108 | A1 | 6/1994 | WO | WO 00/72765 | A1 | 12/2000 |
| WO | WO 94/18893 | A1 | 9/1994 | WO | WO 01/03587 | A1 | 1/2001 |
| WO | WO 94/22378 | A1 | 10/1994 | WO | WO 01/05702 | A1 | 1/2001 |
| WO | WO 94/23659 | A1 | 10/1994 | WO | WO 01/10482 | A1 | 2/2001 |
| WO | WO 95/02369 | A1 | 1/1995 | WO | WO 01/35845 | A1 | 5/2001 |
| WO | WO 95/03743 | A1 | 2/1995 | WO | WO 01/54594 | A1 | 8/2001 |
| WO | WO 95/06817 | A1 | 3/1995 | WO | WO 01/58371 | A1 | 8/2001 |
| WO | WO 95/09576 | A1 | 4/1995 | WO | WO 01/62158 | A2 | 8/2001 |
| WO | WO 95/09577 | A1 | 4/1995 | WO | WO 01/62161 | A1 | 8/2001 |
| WO | WO 95/14436 | A1 | 6/1995 | WO | WO 01/62162 | A1 | 8/2001 |
| WO | WO 95/17855 | A1 | 7/1995 | WO | WO 01/62164 | A2 | 8/2001 |
| WO | WO 95/18383 | A1 | 7/1995 | WO | WO 01/62169 | A1 | 8/2001 |
| WO | WO 95/18572 | A1 | 7/1995 | WO | WO 01/78605 | A2 | 10/2001 |
| WO | WO 95/19739 | A1 | 7/1995 | WO | WO 01/91646 | A1 | 12/2001 |
| WO | WO 95/20360 | A1 | 8/1995 | WO | WO 02/07608 | A2 | 1/2002 |
| WO | WO 95/23557 | A1 | 9/1995 | WO | WO 02/07618 | A1 | 1/2002 |
| WO | WO 95/24865 | A1 | 9/1995 | WO | WO 02/17799 | A1 | 3/2002 |
| WO | WO 95/25471 | A3 | 9/1995 | WO | WO 02/19920 | A1 | 3/2002 |
| WO | WO 95/26562 | A1 | 10/1995 | WO | WO 02/19932 | A1 | 3/2002 |
| WO | WO 95/29639 | A1 | 11/1995 | WO | WO 02/30297 | A2 | 4/2002 |
| WO | WO 96/04858 | A1 | 2/1996 | WO | WO 02/32322 | A2 | 4/2002 |
| WO | WO 96/19151 | A1 | 6/1996 | WO | WO 02/36028 | A1 | 5/2002 |
| WO | WO 96/19152 | A1 | 6/1996 | WO | WO 02/43571 | A2 | 6/2002 |
| WO | WO 96/20652 | A1 | 7/1996 | WO | WO 02/058568 | A1 | 8/2002 |
| WO | WO 96/21119 | A1 | 7/1996 | WO | WO 02/060328 | A1 | 8/2002 |
| WO | WO 96/22055 | A1 | 7/1996 | WO | WO 02/067785 | A1 | 9/2002 |
| WO | WO 96/23448 | A1 | 8/1996 | WO | WO 02/098302 | A1 | 12/2002 |
| WO | WO 96/24301 | A1 | 8/1996 | WO | WO 03/000138 | A2 | 1/2003 |
| WO | WO 96/27337 | A1 | 9/1996 | WO | WO 03/001329 | A2 | 1/2003 |
| WO | WO 96/31155 | A1 | 10/1996 | WO | WO 03/013363 | A1 | 2/2003 |
| WO | WO 96/35464 | A | 11/1996 | WO | WO 03/015604 | A2 | 2/2003 |
| WO | WO 96/39085 | A1 | 12/1996 | WO | WO 03/020106 | A2 | 3/2003 |
| WO | WO 96/39086 | A1 | 12/1996 | WO | WO 03/020139 | A2 | 3/2003 |
| WO | WO 96/39087 | A1 | 12/1996 | WO | WO 03/024339 | A1 | 3/2003 |
| WO | WO 96/39088 | A1 | 12/1996 | WO | WO 03/079909 | A3 | 3/2003 |
| WO | WO 96/39089 | A1 | 12/1996 | WO | WO 03/030743 | A2 | 4/2003 |
| WO | WO 97/00646 | A1 | 1/1997 | WO | WO 03/037193 | A1 | 5/2003 |
| WO | WO 97/00647 | A1 | 1/1997 | WO | WO 03/047436 | A3 | 6/2003 |
| WO | WO 97/06582 | A1 | 2/1997 | WO | WO 03/055402 | A1 | 7/2003 |
| WO | WO 97/10763 | A1 | 3/1997 | WO | WO 03/057048 | A1 | 7/2003 |
| WO | WO 97/10764 | A1 | 3/1997 | WO | WO 03/057058 | A1 | 7/2003 |
| WO | WO 97/11648 | A2 | 4/1997 | WO | WO 03/063694 | A1 | 8/2003 |
| WO | WO 97/11649 | A1 | 4/1997 | WO | WO 03/077769 | A1 | 9/2003 |

| | | | |
|---|---|---|---|
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/117735 A1 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/109125 A1 | 9/2008 |
| WO | WO 2010/063795 A1 | 6/2010 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

European Search Report for 06255759.0, dated Feb. 6, 2009 (7 pages).

International Search Report for PCT/US2011/021051, dated May 31, 2011 (4 pages).

\* cited by examiner

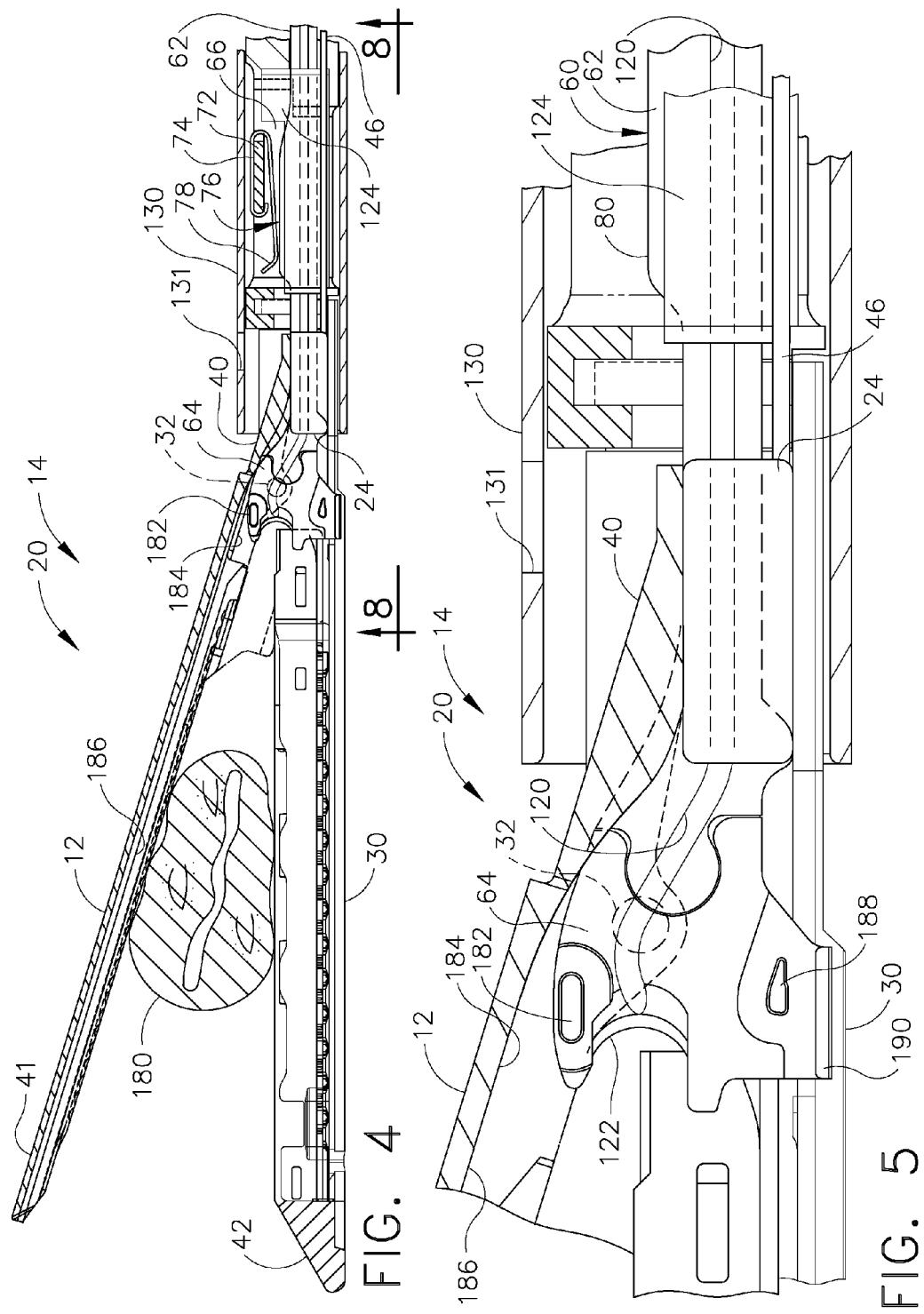

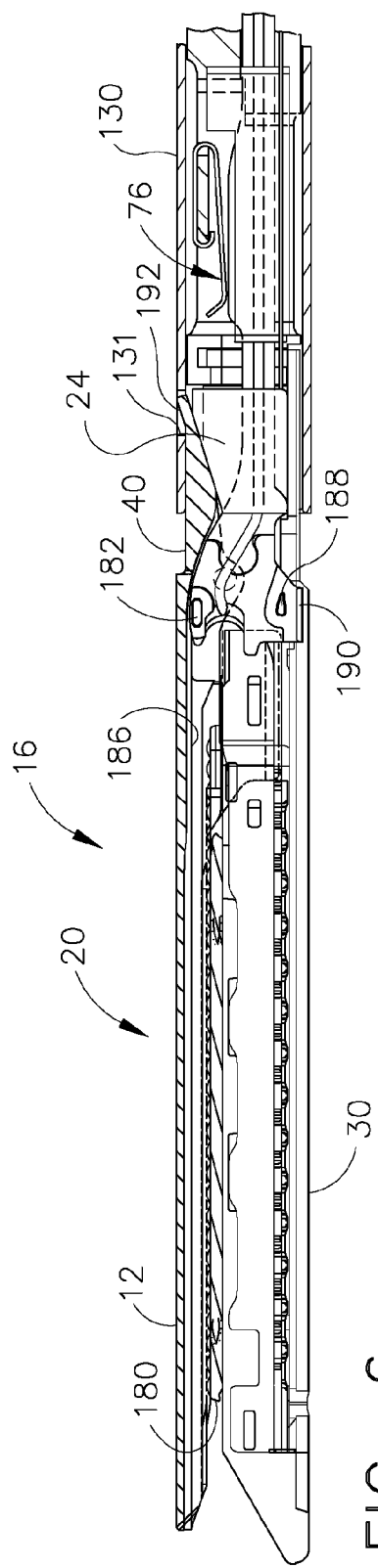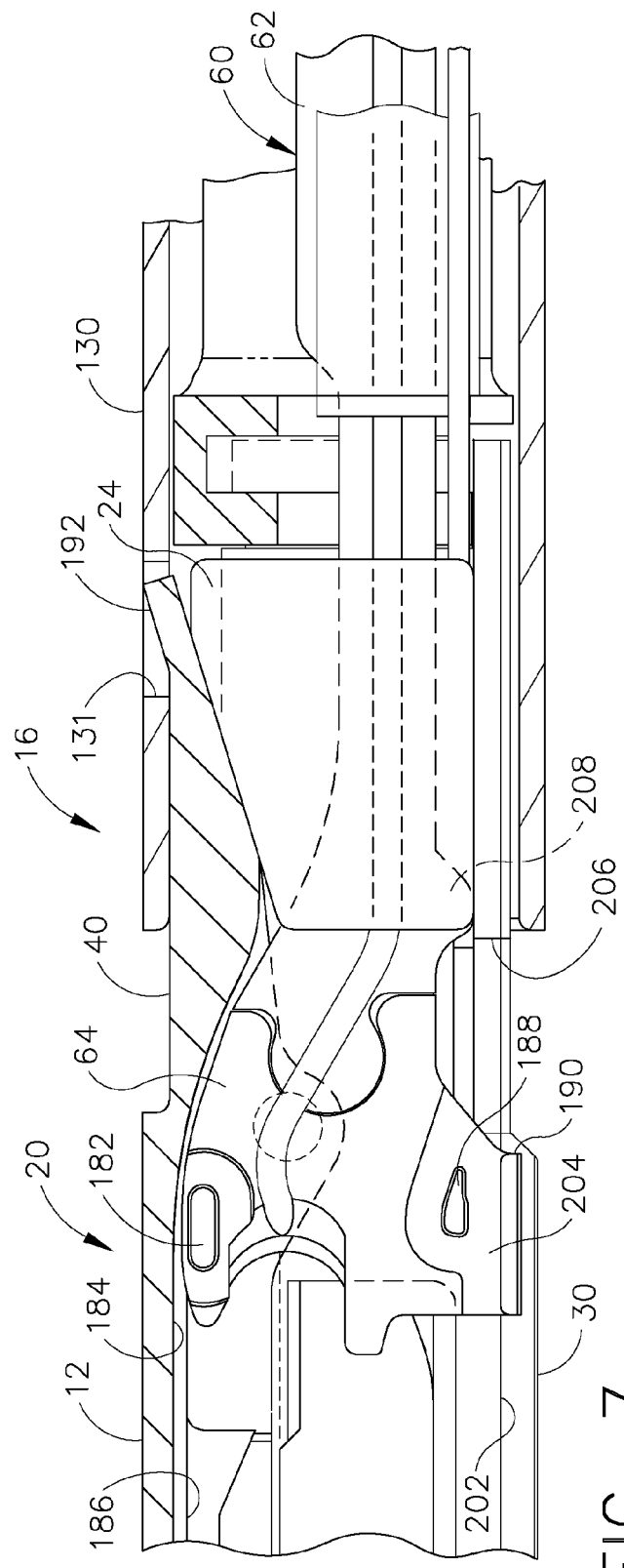

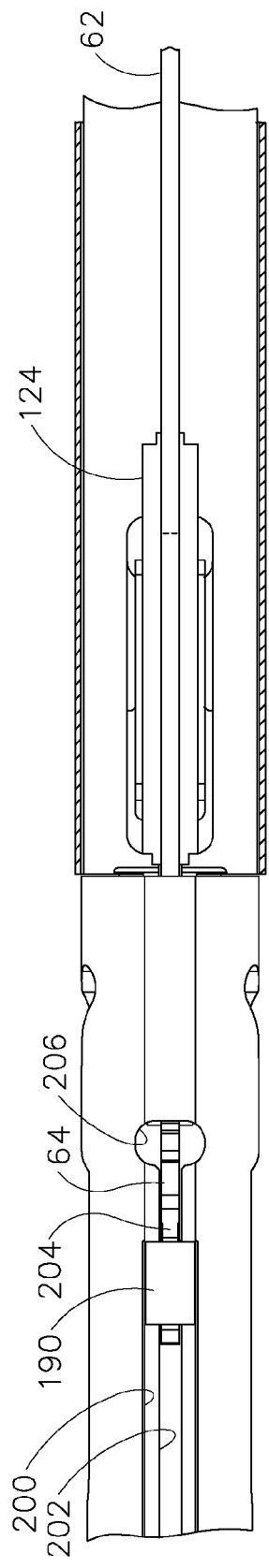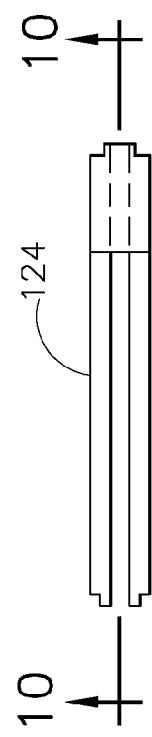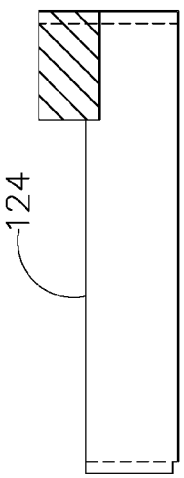
FIG. 8
FIG. 9
FIG. 10

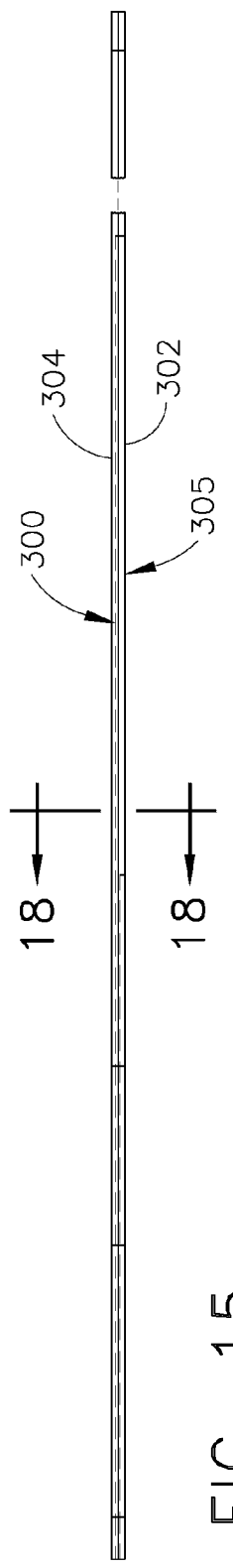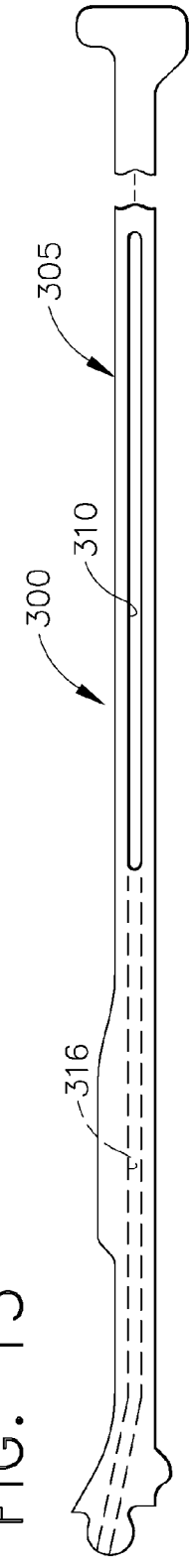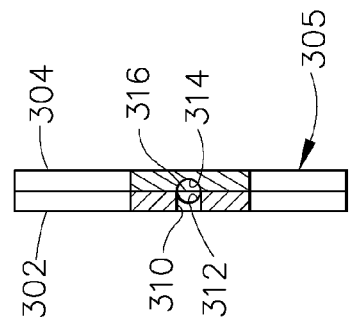
FIG. 15
FIG. 16
FIG. 17
FIG. 18

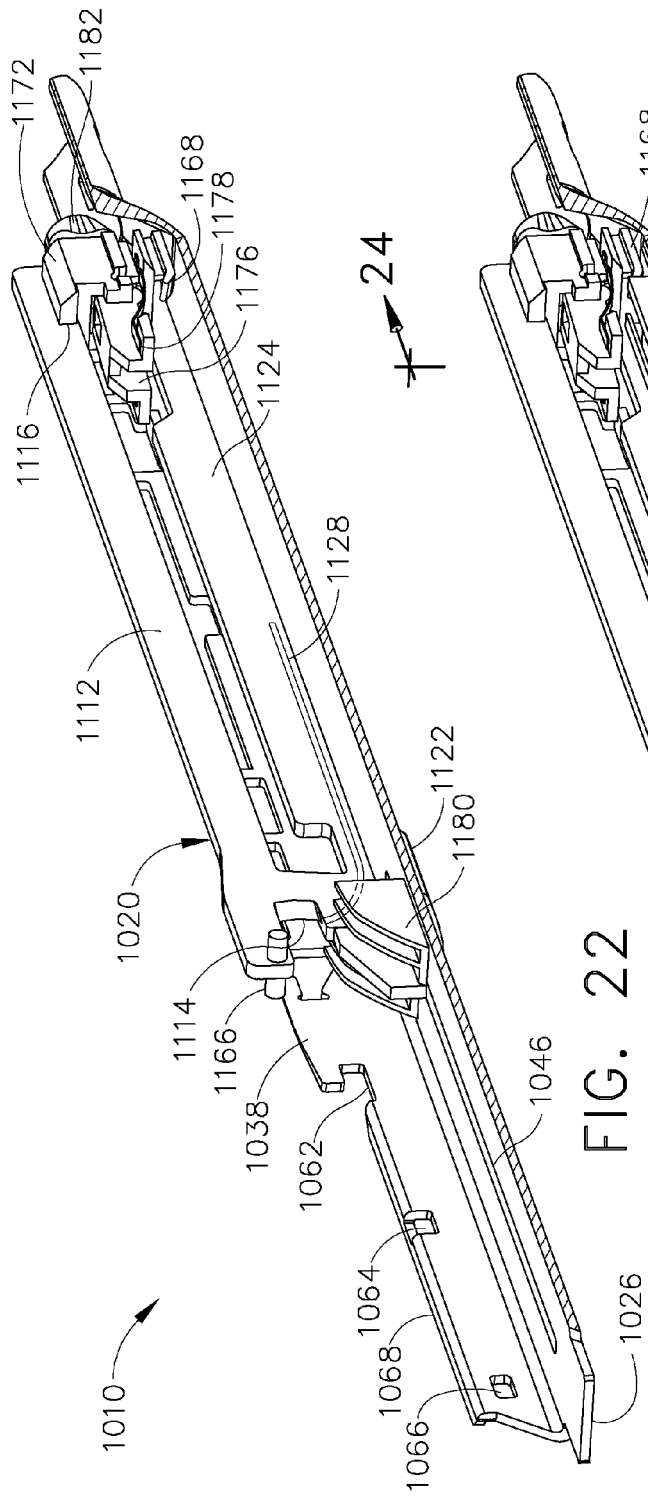
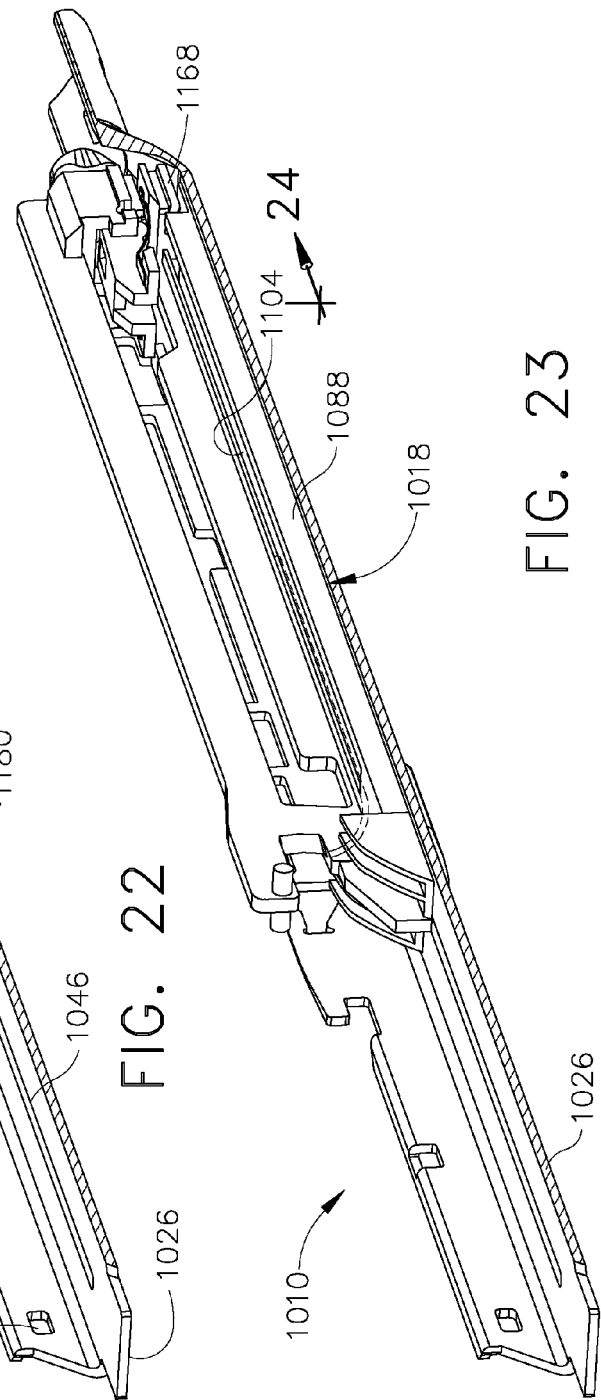

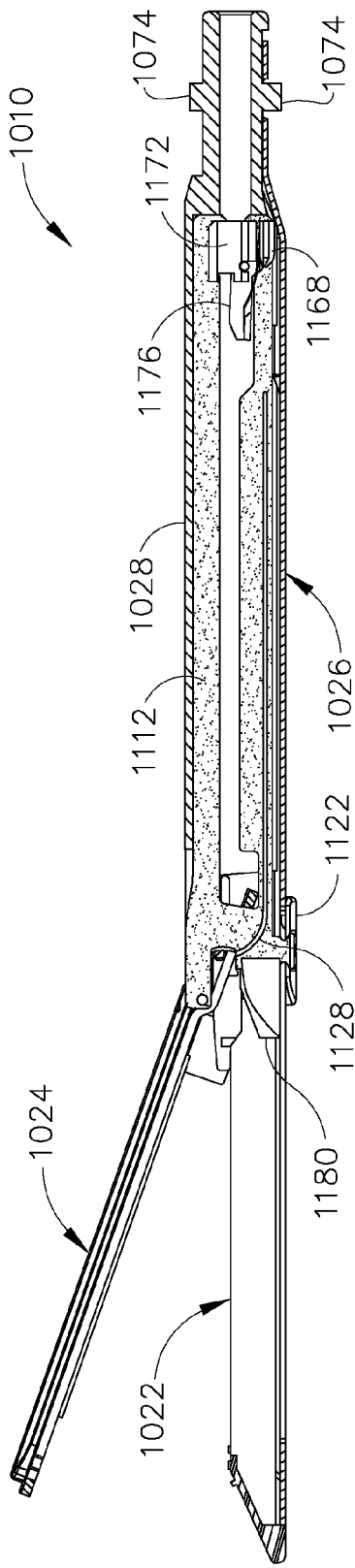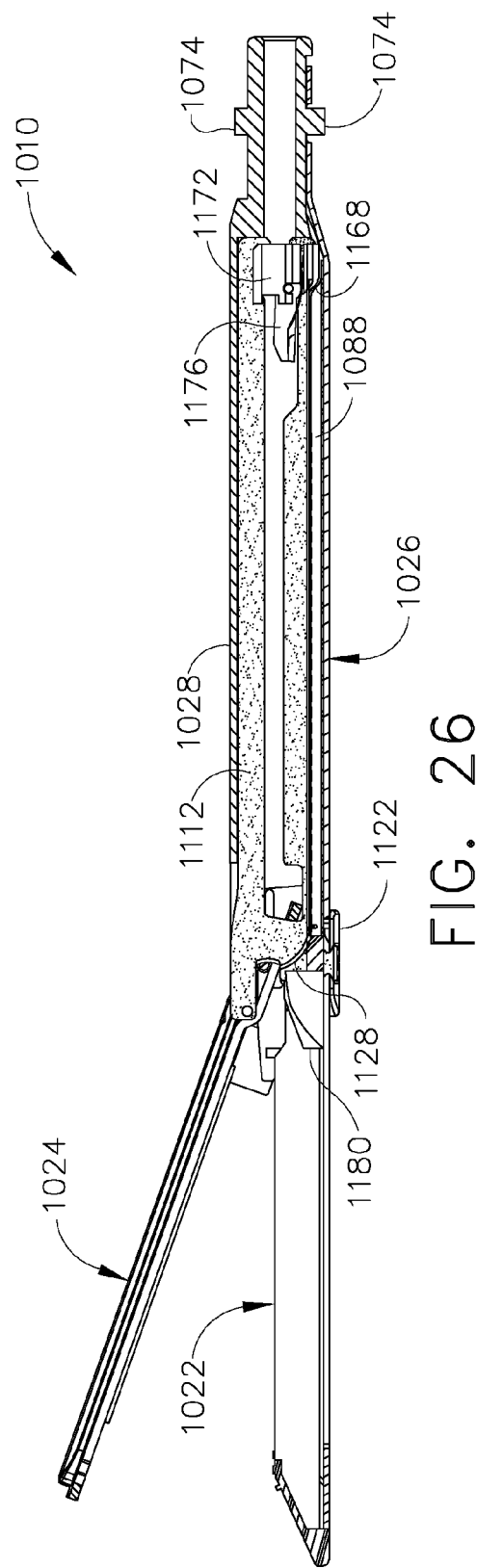

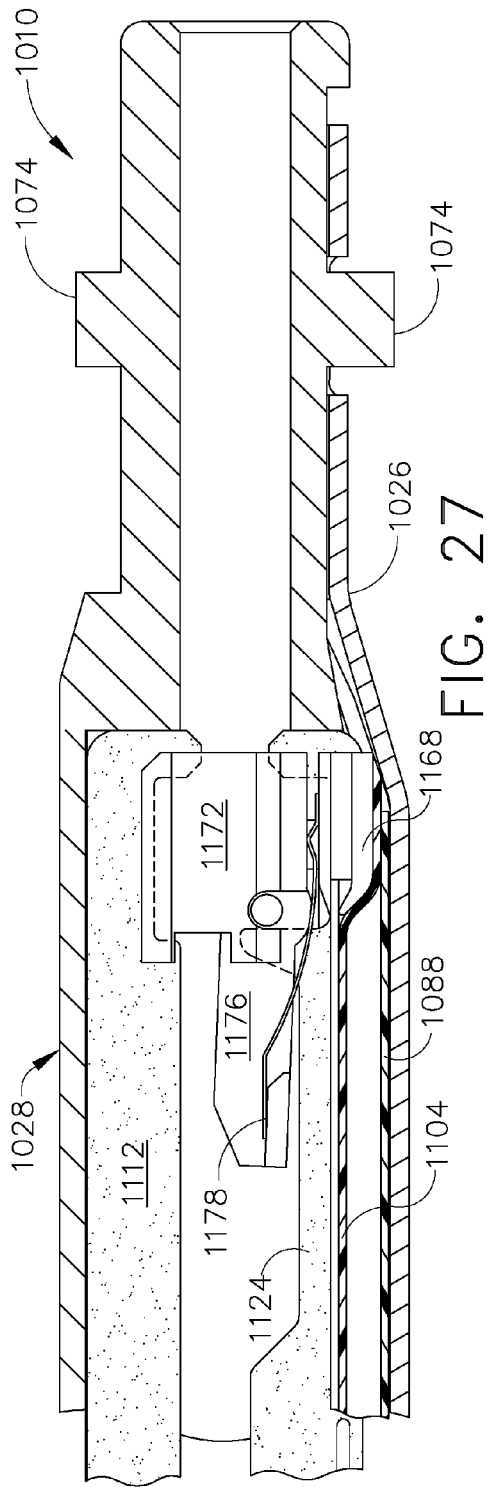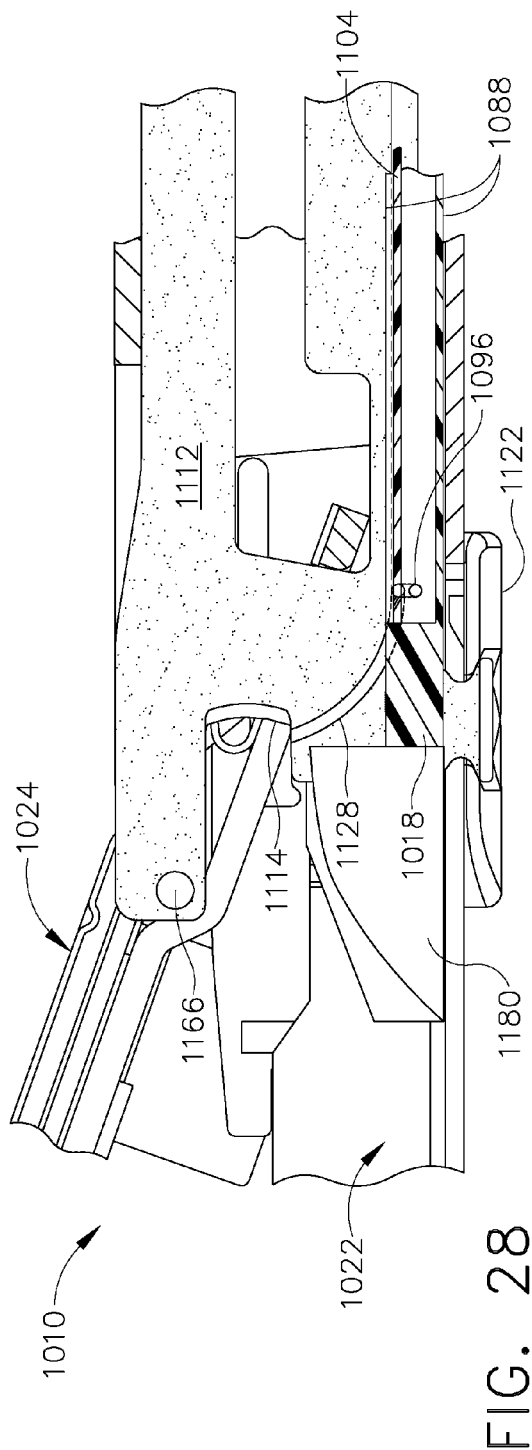

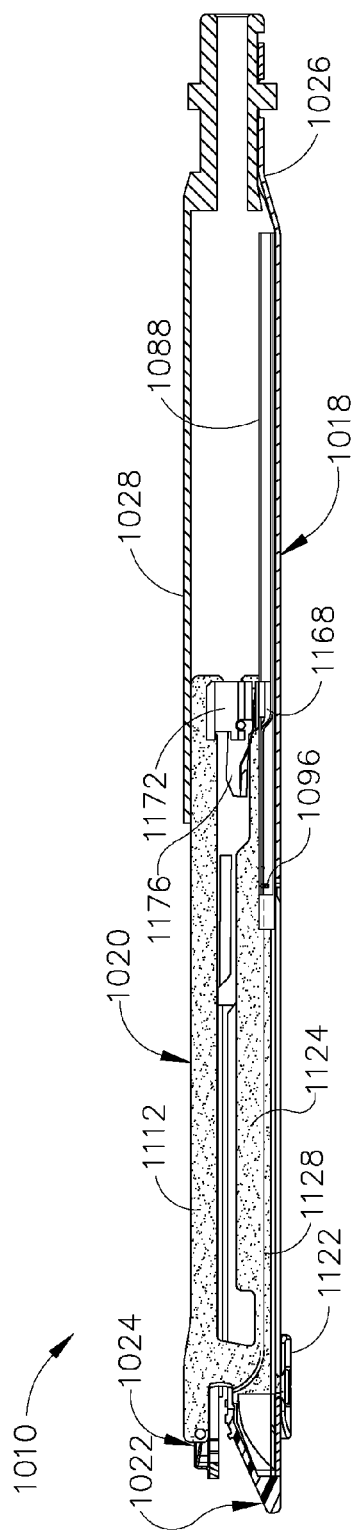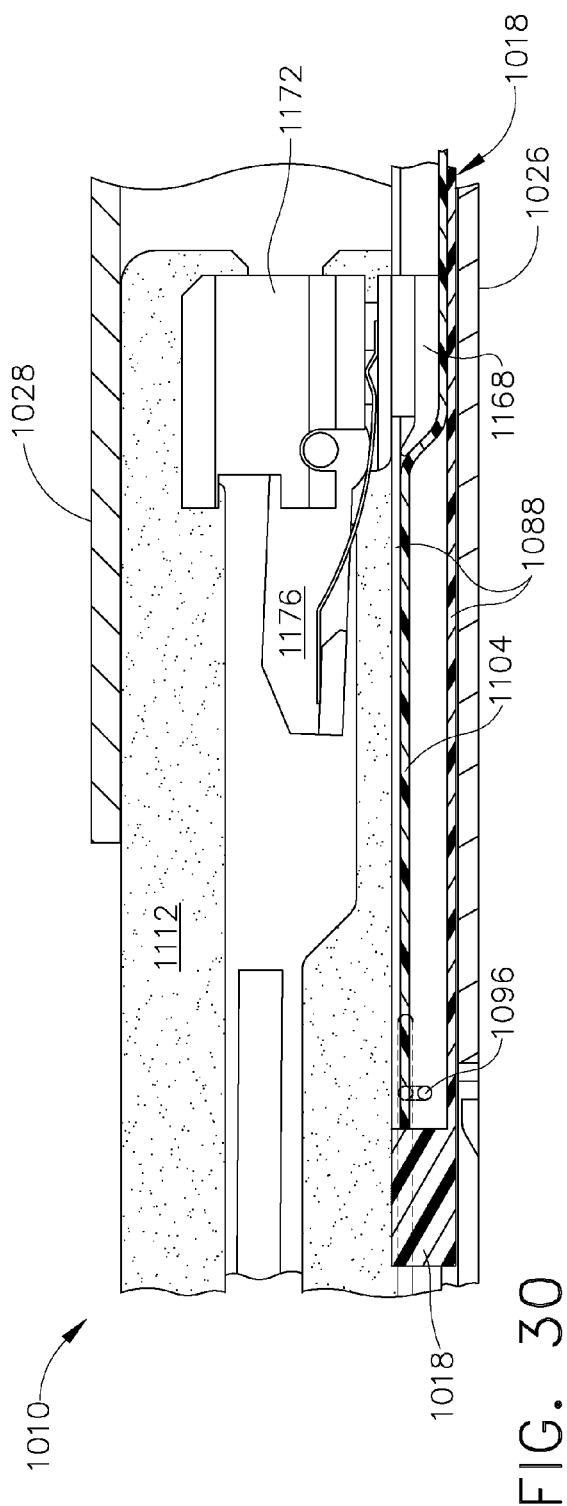

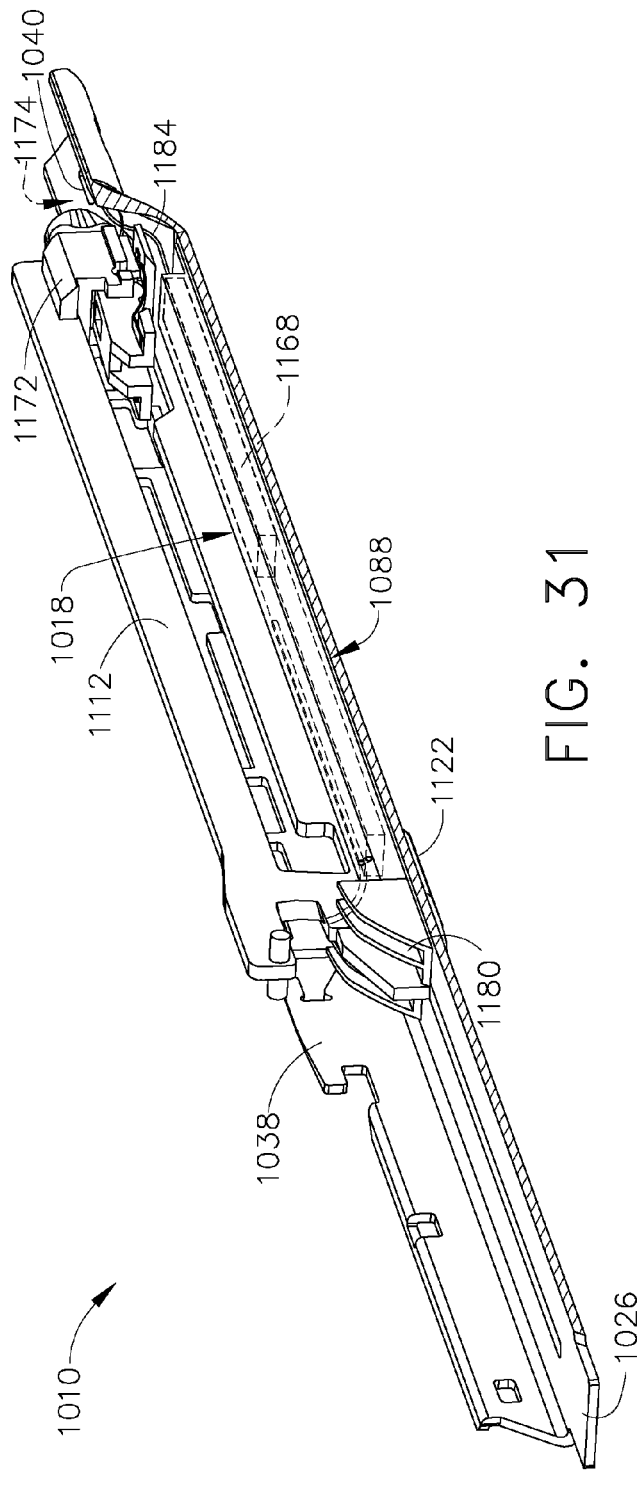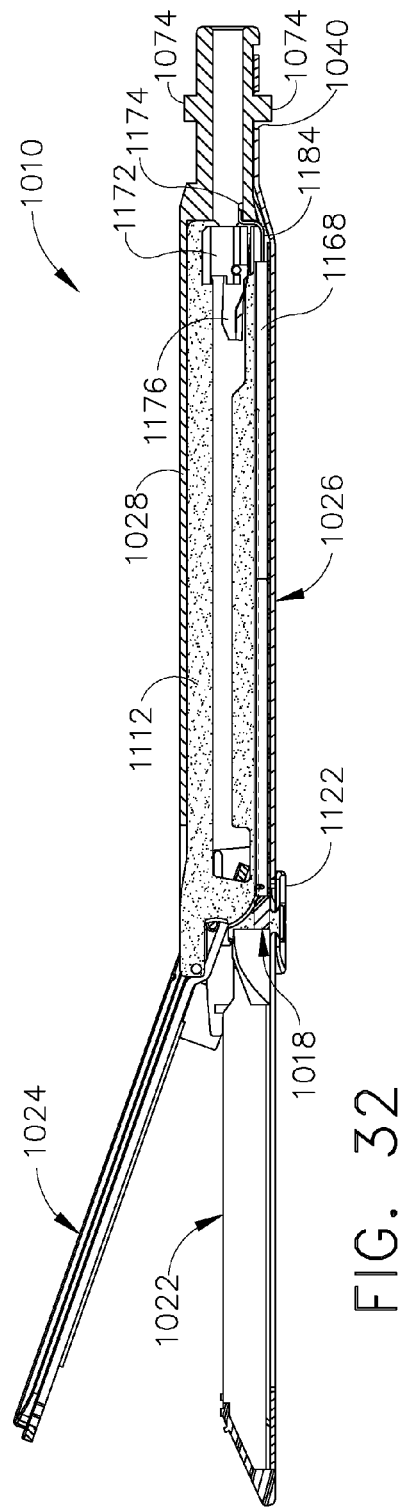
FIG. 31
FIG. 32

SURGICAL STAPLING INSTRUMENT HAVING A MEDICAL SUBSTANCE DISPENSER

CROSS REFERENCE TO RELATED APPLICATIONS

The present application is a continuation-in-part application claiming priority under 35 U.S.C. §120 from U.S. patent application Ser. No. 11/141,753, entitled SURGICAL STAPLING INSTRUMENT HAVING AN ELECTROACTIVE POLYMER ACTUATED MEDICAL SUBSTANCE DISPENSER, filed on Jun. 1, 2005, U.S. Patent Publication No. 2006/0025813, which claims the benefit under 35 U.S.C. §119(e) of U.S. Provisional Application Ser. No. 60/591,694, entitled SURGICAL INSTRUMENT INCORPORATING AN ELECTRICALLY ACTUATED ARTICULATION MECHANISM, filed Jul. 28, 2004, the entire disclosures of which are incorporated by reference herein. The present application is also a continuation-in-part application claiming priority under 35 U.S.C. §120 from U.S. patent application Ser. No. 11/731,521, entitled DISPOSABLE LOADING UNIT AND SURGICAL INSTRUMENTS INCLUDING SAME, filed on Mar. 30, 2007, U.S. Patent Publication No. 2007/0170225, now abandoned which is a continuation application of U.S. patent application Ser. No. 11/271,234, entitled DISPOSABLE LOADING UNIT AND SURGICAL INSTRUMENTS INCLUDING SAME, filed on Nov. 10, 2005, which issued as U.S. Pat. No. 7,354,447 on Apr. 8, 2008, the entire disclosures of which are incorporated by reference herein.

BACKGROUND

The present application relates in general to surgical stapler instruments that are capable of applying lines of staples to tissue while cutting the tissue between those staple lines and, more particularly, to improvements relating to stapler instruments and improvements in processes for forming various components of such stapler instruments. This application also discloses devices that are related, generally and in various embodiments, to a disposable loading unit configured for connection to a reusable surgical instrument, and to surgical instruments that include a disposable loading unit.

Surgical instruments that are utilized to concurrently make longitudinal incisions in tissue and apply lines of staples on opposing sides of the incisions are known in the art. The tissue may include, for example, human tissue, animal tissue, membranes, or other organic substances. Such surgical instruments commonly include a pair of opposing jaw members that cooperate to grasp or clamp the tissue therebetween and a cutting surface that makes the incision. When employed in endoscopic or laparoscopic applications, the opposing jaw members are capable of passing through a cannula passageway. One of the jaw members typically supports a staple cartridge having at least two laterally spaced rows of staples and pushers aligned with the staples. The other jaw member is movable between an open position and a closed position, and defines an anvil having staple-forming pockets correspondingly aligned with the rows of staples in the staple cartridge. Such instruments may also include a wedge that, when driven, sequentially contacts the pushers to effect the firing of the staples toward the anvil and through the tissue.

An example of a surgical stapler suitable for endoscopic applications, described in U.S. Pat. No. 5,465,895, advantageously provides distinct closing and firing actions. Thereby, a clinician is able to close the jaw members upon tissue to position the tissue prior to firing. Once the clinician has determined that the jaw members are properly gripping tissue, the clinician can then fire the surgical stapler, thereby severing and stapling the tissue. The simultaneous severing and stapling avoids complications that may arise when performing such actions sequentially with different surgical tools that respectively only sever or staple.

However, the trauma caused to the tissue with such actions can be significant. In general, the delivery of sufficient amounts of medical agents to the site of the traumatized tissue promotes the proper sealing of the incision, reduces the possibility of infection, and/or significantly improves the healing process. The application of medical agents to the site of the traumatized tissue is often accomplished by means other than the surgical instrument that makes the incision and applies the staples. Such means generally increase the complexity and cost associated with the procedure. However, such means are often necessary because many of the surgical instruments utilized to concurrently make the incision and apply the staples are not configured to store and deliver sufficient amounts of medical agents to the site of the traumatized tissue, and the delivery of some medical agents to the site of the traumatized tissue via the surgical instrument would render the surgical instrument unsuitable for reuse.

The foregoing discussion is intended only to illustrate the present field and should not be taken as a disavowal of claim scope.

SUMMARY

In various embodiments, an assembly of a surgical instrument is provided. In at least one embodiment, the assembly can comprise a housing, a cutting member relatively movable with respect to the housing, and an agent cartridge connected to the housing. In these embodiments, the cutting member can comprise a cutting surface, a body including a first surface, and a groove at least partially defined by the first surface. Further, in these embodiments, the agent cartridge can include a cavity configured to house a medical agent therein. Additionally, in these embodiments, the cutting member groove can be in fluid communication with the cavity. Moreover, in these embodiments, the groove can be configured to deliver the medical agent from the cavity proximate to the cutting surface.

In at least one embodiment, an assembly of a surgical instrument is provided that can comprise a housing, a member relatively movable with respect to the housing, and an agent cartridge. In these embodiments, the member can comprise a cutting surface, a body including a first surface, and a passage at least partially defined by the first surface. Further, in these embodiments, the agent cartridge can include a medical agent storage portion configured to house a medical agent therein. Additionally, in these embodiments, the member passage can be in fluid communication with the medical agent storage portion. Moreover, in these embodiments, the passage can be configured to deliver the medical agent from the medical agent storage portion proximate to the cutting surface.

In various embodiments, a surgical instrument is provided. In at least one embodiment, the surgical instrument can comprise a frame, a member relatively movable with respect to the frame, and an agent cartridge. In these embodiments, the member can comprise a cutting surface, a body including a first surface, and a groove at least partially defined by the first surface. Further, in these embodiments, the agent cartridge can include a medical agent storage portion configured to house a medical agent therein. Additionally, in these embodiments, the member groove can be in fluid communication with the medical agent storage portion. Moreover, in these embodiments, the groove can be configured to deliver the medical agent from the medical agent storage portion proximate to the cutting surface.

BRIEF DESCRIPTION OF THE FIGURES

The novel features of the embodiments described herein are set forth with particularity in the appended claims. The embodiments, however, both as to organization and methods of operation may be better understood by reference to the following description, taken in conjunction with the accompanying drawings as follows.

FIG. 4 is a left side detail view in elevation of a distal portion of the implement portion of the surgical stapling and severing instrument of FIG. 1 taken in cross section generally through the longitudinal axis thereof but showing a laterally offset fluid bladder actuator opening the anvil.

FIG. 5 is a left side detail view of an E-beam firing bar incorporating medical substance ducting.

FIG. 6 is a left side detail view in elevation of the distal portion of the implement portion of the surgical stapling and severing instrument of FIG. 4 taken in cross section generally through the longitudinal axis thereof with the anvil closed.

FIG. 7 is a left side detail view of the E-beam firing bar of FIG. 6.

FIG. 8 is a top detail view of a joined portion of a lower jaw (staple channel) of the end effector and elongate shaft taken in cross section through the lines 8-8 depicting guidance to the E-beam firing bar.

FIG. 9 is a front view of a firing bar guide of the implement portion of the surgical stapling and severing instrument of FIG. 2.

FIG. 10 is a left side view of the firing bar guide of FIG. 9 taken in cross section along lines 9-9.

FIG. 15 is a top view of the firing bar of the surgical stapling and severing instrument of FIG. 2.

FIG. 16 is a left side view of a laminate firing bar showing an internal fluid path in phantom for the surgical stapling and severing instrument of FIG. 1.

FIG. 17 is a left side detail view of an alternate E-beam showing an internal fluid path in phantom showing an internal fluid path in phantom.

FIG. 18 is a front view in elevation of the laminate firing bar of FIG. 15 taken in cross section along line 18-18 through a proximal open groove of a fluid path.

FIG. 22 illustrates various embodiments of a disposable loading unit.

FIG. 23 illustrates various embodiments of a disposable loading unit.

FIG. 25 illustrates various embodiments of a disposable loading unit.

FIG. 26 illustrates various embodiments of a disposable loading unit.

FIG. 27 illustrates various embodiments of a disposable loading unit.

FIG. 28 illustrates various embodiments of a disposable loading unit.

FIG. 29 illustrates various embodiments of a disposable loading unit.

FIG. 30 illustrates various embodiments of a disposable loading unit.

FIG. 31 illustrates various embodiments of a disposable loading unit.

FIG. 32 illustrates various embodiments of a disposable loading unit.

DETAILED DESCRIPTION

It is to be understood that the figures and descriptions of the disclosed embodiments have been simplified to illustrate elements that are relevant for a clear understanding of the disclosed embodiments, while eliminating, for purposes of clarity, other elements. Those of ordinary skill in the art will recognize, however, that these and other elements may be desirable. However, because such elements are well known in the art, and because they do not facilitate a better understanding of the disclosed embodiments, a discussion of such elements is not provided herein.

Certain embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of these embodiments is defined solely by the claims. The features illustrated or described in connection with one embodiment may be combined with the features of other embodiments. Further, where an ordering of steps in a process is indicated, such ordering may be rearranged or the steps may be carried out contemporaneously as desired unless illogical or the listed order is explicitly required. Such modifications and variations are intended to be included within the scope of the appended claims.

Also, in the following description, it is to be understood that terms such as "forward," "rearward," "front," "back," "right," "left," "over," "under," "top," "bottom," "upwardly,"

"downwardly," "proximally," "distally," and the like are words of convenience and are not to be construed as limiting terms. The description below is for the purpose of describing various embodiments and is not intended to limit the appended claims.

Figure 1:
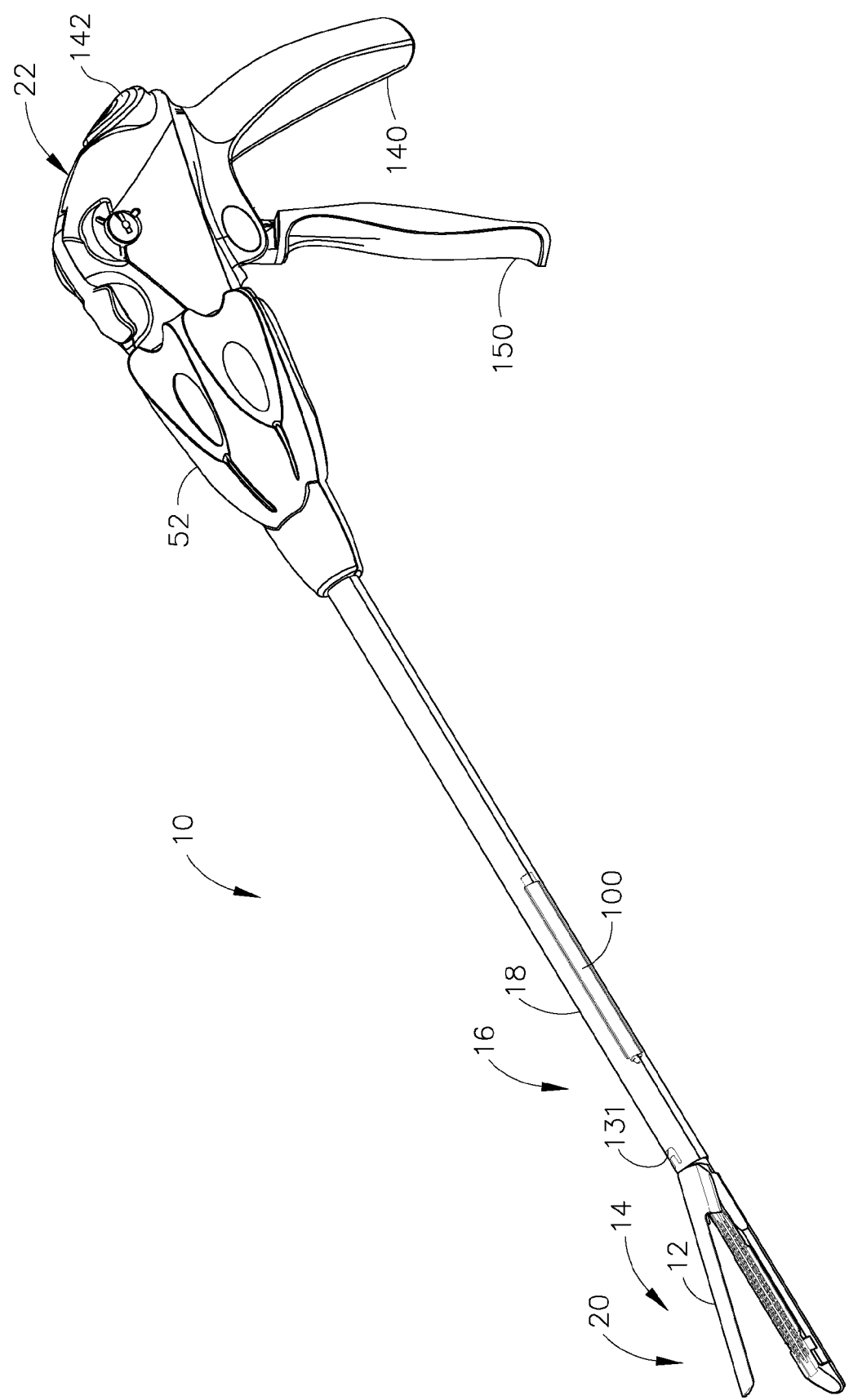
FIG. 1 is a perspective view of a surgical stapling and severing instrument having a fluid actuated upper jaw (anvil) in an open position and an electroactive polymer (EAP) medical substance dispensing shaft.
Figure 2:
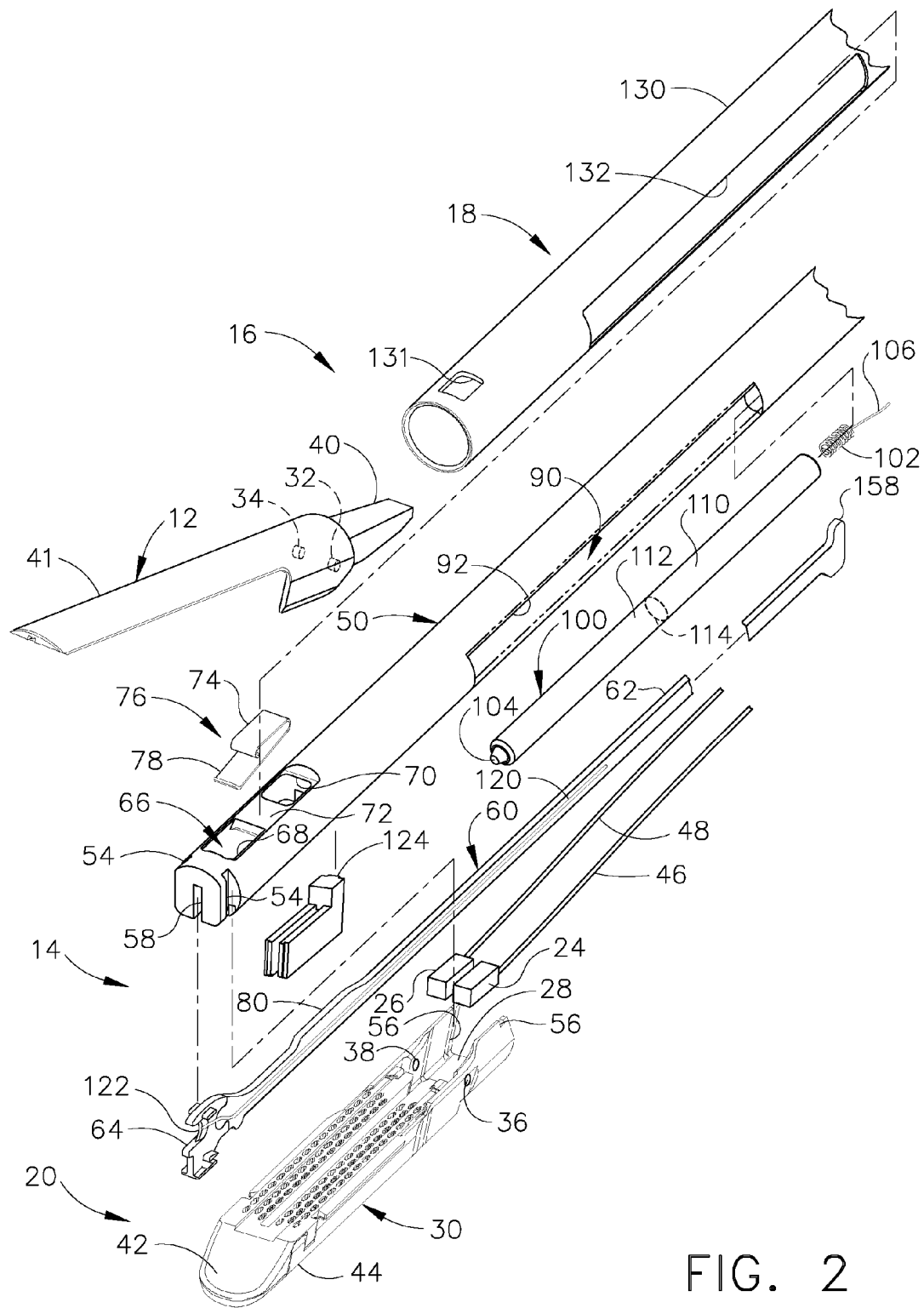
FIG. 2 is a disassembled perspective view of an implement portion of the surgical stapling and severing instrument of FIG. 1.

Turning to the drawings, wherein like numerals denote like components throughout the several views, in FIGS. 1-2, a surgical stapling and severing instrument 10 that is capable of practicing the unique benefits of at least one embodiment, including both fluid actuation (e.g., opening, closing/clamping) of an upper jaw (anvil) 12 of an end effector 14 as well as dispensing a medical substance onto tissue as severed. Fluid actuation of the end effector 14 provides a range of design options that avoid some design limitations of traditional mechanical linkages. For example, instances of binding or component failure may be avoided. Further, dispensing liquids onto severed tissue allows for a range of advantageous therapeutic treatments to be applied, such as the application of anesthetics, adhesives, cauterizing substances, antibiotics, coagulant, etc.

With particular reference to FIG. 2, the surgical stapling and severing instrument 10 includes an implement portion 16 formed by an elongate shaft 18 and the end effector 14, depicted as a stapling assembly 20. The surgical stapling and severing instrument 10 also includes a handle 22 (FIG. 1) attached proximally to the shaft 18. The handle 22 remains external to the patient as the implement portion 16 is inserted through a surgical opening, or especially a cannula of a trocar that forms a pneumoperitoneum for performing a minimally invasive surgical procedure.

Left and right fluid bladders (lift bags) 24, 26 are supported within an aft portion 28 of a staple channel 30. The anvil 12 includes a pair of inwardly directed lateral pivot pins 32, 34 that pivotally engage outwardly open lateral pivot recesses 36, 38 formed in the staple channel 30 distal to the aft portion 28. The anvil 12 includes a proximally directed lever tray 40 that projects into the aft portion 28 of the staple channel 30 overtop and in contact with the fluid bladders (lift bags) 24, 26 such that filling the fluid bladders 24, 26 causes a distal clamping section 41 of the anvil 12 to pivot like a teeter-totter toward a staple cartridge 42 held in a distal portion 44 of the staple channel 30. Evacuation and collapse of the fluid bladders 24, 26, or some other resilient feature of the end effector 14, causes the anvil 12 to open. Left and right fluid conduits 46, 48 communicate respectively with the left and right fluid bladders 24, 26 to bi-directionally transfer fluid for actuation. It should be appreciated that applications consistent with the present embodiment may include a mechanical actuation in the handle 22 (e.g., closure trigger) (not shown) wherein the user depresses a control that causes closure and clamping of the end effector 12.

It will be appreciated that the terms "proximal" and "distal" are used herein with reference to a clinician gripping a handle of an instrument. Thus, the staple applying assembly 20 is distal with respect to the more proximal handle 22. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

With particular reference to FIG. 2, the elongate shaft 18 includes a frame 50 whose proximal end is rotatably engaged to the handle 22 (FIG. 1) such that a rotation knob 52 rotates the frame 50 along with the end effector 14. A distal end of the frame 50 has lateral recesses 54 that engage a proximal lip 56 of the staple channel 30. The frame 50 includes a laterally centered, bottom firing slot 58 that passes longitudinally through the frame 50 for receiving a two-piece firing bar 60 comprised of a firing bar 62 with a distally attached E-beam 64, the latter translating within the staple applying assembly 20 to sever and staple tissue. A distal portion of the frame 50 includes an upper cavity 66 whose distal and proximal ends communicate through distal and proximal apertures 68, 70, defining there between a cross bar 72 over which a distally projecting clip 74 of a clip spring 76 engages with a lower spring arm 78, distally and downwardly projecting through the upper cavity 66 to bias the firing bar 62 downwardly into engagement with the staple channel 30, especially when the lower spring arm 78 encounters a raised portion 80 on the firing bar 62.

Medical substance dispensing is integrated into the elongate shaft 18 by including a laterally offset cylindrical cavity 90 formed in the frame 50 that communicates along its longitudinal length to the outside via a rectangular aperture 92 that is slightly shorter than an electroactive polymer (EAP) syringe 100 that is inserted through the aperture 92 into the cylindrical cavity 90. A proximal portion of the cylindrical cavity 90 contains a longitudinally aligned compression spring 102 that urges a distal dispensing cone 104 of the EAP syringe 100 distally into sealing contact with the frame 50 and allows translation for insertion and removal of the EAP syringe 100. An electrical conductor 106 passes through the frame 50 and is attached to the compression spring 102, which is also formed of an electrically conductive metal. An aft portion of the EAP syringe 100 is conductive and contacts the spring 102 to form a cathode to an EAP actuator 110 held in a proximal portion of the EAP syringe 100. It will be appreciated that another conductor, perhaps traveling with the conductor 106, also electrically communicates to the EAP actuator 110 to serve as the anode.

When activated, the EAP actuator 110 longitudinally expands, serving as a plunger to dispel a medical substance 112 in a distal portion of the EAP syringe 100 through the distal dispensing cone 104. Insofar as the EAP actuator 110 laterally contracts to compensate for its longitudinal expansion, a plunger seal 114 maintains a transverse seal within the EAP syringe 100. An vent (not shown), such as around conductor 106 allows air to refill the EAP syringe 100 behind the plunger seal 114 as the medical substance 112 is dispensed. The vent may rely upon the surface tension of the medical substance 112 to avoid leaking or be a one-way valve. As described below, the medical substance 112 is conducted by the frame 50 to a lateral fluid groove 120 that is formed in the firing bar 62 and the E-beam 64 to direct the medical substance to a cutting surface 122 of the E-beam 64. The frame slot 58 is sized to seal the lateral fluid groove 120. The portion of the lateral fluid groove 120 that is positioned under the spring clip 76 is sealed by a firing bar guide 124. In the illustrative version, an outer sheath 130 encompasses the frame 50 and proximally projecting lever tray 40 of the anvil 12. A top distal opening 131 allows closing of the anvil 12.

An outer rectangular aperture 132 of the outer sheath 130 is sized and longitudinally positioned to correspond to the rectangular aperture 92 formed in frame 50. In some applications, the outer sheath 130 may be rotated to selectively align the rectangular aperture 92 with the outer rectangular aperture 132 for insertion or removal of the EAP syringe 100. It should be appreciated that in some applications that the EAP syringe 100 may be integrally assembled into an elongate shaft that does not allow for selecting a desired medical substance. For instance, a disposable implement portion with an integral staple cartridge and medical dispensing reservoir may be selected by the clinician as a unit. It is believed that allowing insertion at the time of use, though, has certain advantages including clinical flexibility in selecting a medical substance (e.g., anesthetics, adhesives, antibiotics, cauterizing compound, etc.) and extending the shelf life/simplifying storage and packaging of the implement portion 16.

In the illustrative version, an elongate stack of many disk-shaped EAP layers are aligned longitudinally and configured to expand along this longitudinal axis. Electroactive polymers (EAPs) are a set of conductive doped polymers that change shape when electrical voltage is applied. In essence, the conductive polymer is paired to some form of ionic fluid or gel and electrodes. Flow of the ions from the fluid/gel into or out of the conductive polymer is induced by the voltage potential applied and this flow induces the shape change of the polymer. The voltage potential ranges from IV to 4 kV, depending on the polymer and ionic fluid used. Some of the EAPs contract when voltage is applied and some expand. The EAPs may be paired to mechanical means such as springs or flexible plates to change the effect that is caused when the voltage is applied.

There are two basic types of EAPs and multiple configurations of each type. The two basic types are a fiber bundle and a laminate version. The fiber bundle consists of fibers around 30-50 microns. These fibers may be woven into a bundle much like textiles and are often called EAP yarn because of this. This type of EAP contracts when voltage is applied. The electrodes are usually made up of a central wire core and a conductive outer sheath that also serves to contain the ionic fluid that surrounds the fiber bundles. An example of a commercially available fiber EAP material, manufactured by Santa Fe Science and Technology and sold as PANION™ fiber, is described in U.S. Pat. No. 6,667,825, which is hereby incorporated by reference in its entirety.

The other type is a laminate structure, which consists of a layer of EAP polymer, a layer of ionic gel and two flexible plates that are attached to either side of the laminate. When a voltage is applied, the square laminate plate expands in one direction and contracts in the perpendicular direction. An example of a commercially available laminate (plate) EAP material is from Artificial Muscle Inc, a division of SRI Laboratories. Plate EAP material is manufactured by EAMEX of Japan and is referred to as thin film EAP.

It should be noted that EAPs do not change volume when energized; they merely expand or contract in one direction while doing the opposite in the transverse direction. The laminate version may be used in its basic form by containing one side against a rigid structure and using the other much like a piston. The laminate version may also be adhered to either side of a flexible plate. When one side of the flexible plate EAP is energized, it expands flexing the plate in the opposite direction. This allows the plate to be flexed in either direction, depending on which side is energized.

An EAP actuator usually consists of numerous layers or fibers bundled together to work in cooperation. The mechanical configuration of the EAP determines the EAP actuator and its capabilities for motion. The EAP may be formed into long stands and wrapped around a single central electrode. A flexible exterior outer sleeve will form the other electrode for the actuator as well as contain the ionic fluid necessary for the function of the device. In this configuration when the electrical field is applied to the electrodes, the strands of EAP shorten. This configuration of EAP actuator is called a fiber EAP actuator. Likewise, the laminate configuration may be placed in numerous layers on either side of a flexible plate or merely in layers on itself to increase its capabilities. Typical fiber structures have an effective strain of 2-4% where the typical laminate version achieves 20-30%, utilizing much higher voltages.

For instance, a laminate EAP composite may be formed from a positive plate electrode layer attached to an EAP layer, which in turn is attached to an ionic cell layer, which in turn is attached to a negative plate electrode layer. A plurality of laminate EAP composites may be affixed in a stack by adhesive layers there between to form an EAP plate actuator. It should be appreciated that opposing EAP actuators may be formed that can selectively bend in either direction.

A contracting EAP fiber actuator may include a longitudinal platinum cathode wire that passes through an insulative polymer proximal end cap through an elongate cylindrical cavity formed within a plastic cylinder wall that is conductively doped to serve as a positive anode. A distal end of the platinum cathode wire is embedded into an insulative polymer distal end cap. A plurality of contracting polymer fibers are arranged parallel with and surrounding the cathode wire and have their ends embedded into respective end caps. The plastic cylinder wall is peripherally attached around respective end caps to enclose the cylindrical cavity to seal in ionic fluid or gel that fills the space between contracting polymer fibers and cathode wire. When a voltage is applied across the plastic cylinder wall (anode) and cathode wire, ionic fluid enters the contracting polymer fibers, causing their outer diameter to swell with a corresponding contraction in length, thereby drawing the end caps toward one another.

Returning to FIG. 1, the handle 22 controls closure of the anvil 12, firing of the two-piece firing bar 60 (FIG. 2), and dispensing of the medical substance. In an illustrative version, a pistol grip 140 may be grasped and a thumb button 142 depressed as desired to control closure of the anvil 12. The thumb button 142 provides a proportional electrical signal to an EAP dispensing actuator not shown) similar to the EAP syringe 100 to transfer fluid through the conduits 46, 48 to the fluid bladders 24, 26 to close the anvil 12 (FIG. 2). When the thumb button 142 is fully depressed, a mechanical toggle lock (not shown) engages to hold the thumb button 142 down until a full depression releases the toggle lock for releasing the thumb button 142. Thus, when the thumb button 142 is held down, the surgeon has a visual indication that the end effector 14 is closed and clamped, which may be maintained in this position by continued activation of an EAP dispensing actuator or by a locking feature. For instance, control circuitry may sense movement of the thumb button 142, causing a normally closed EAP shutoff valve (not shown) to open that communicates between the EAP dispensing actuator and the conduits 46, 48. Once movement ceases, the EAP shutoff valve is allowed to close again, maintaining the anvil 12 position. In addition, a manual release could be incorporated to defeat such a lockout to open the anvil 12.

As an alternative, a closure trigger (not shown) or other actuator may be included that bi-directionally transfers fluid to the fluid bladders 24, 26 as described in commonly owned U.S. patent application Ser. No. 11/061,908 entitled "SURGICAL INSTRUMENT INCORPORATING A FLUID TRANSFER CONTROLLED ARTICULATION MECHANISM" to Kenneth Wales and Chad Boudreaux, filed on 18 Feb. 2005, the disclosure of which is hereby incorporated by reference in its entirety. A number of such fluid actuators for articulation of a pivoting shaft are described that may be adapted for closing the anvil 12. To take full advantage of the differential fluid transfer described for several of these versions, it should be appreciated that an opposing lift bag (not shown) may be placed above the lever tray 40 of the anvil 12 to assert an opening force as the left and right fluid bladders (lift bags) 24, 26 collapse.

Figure 3:
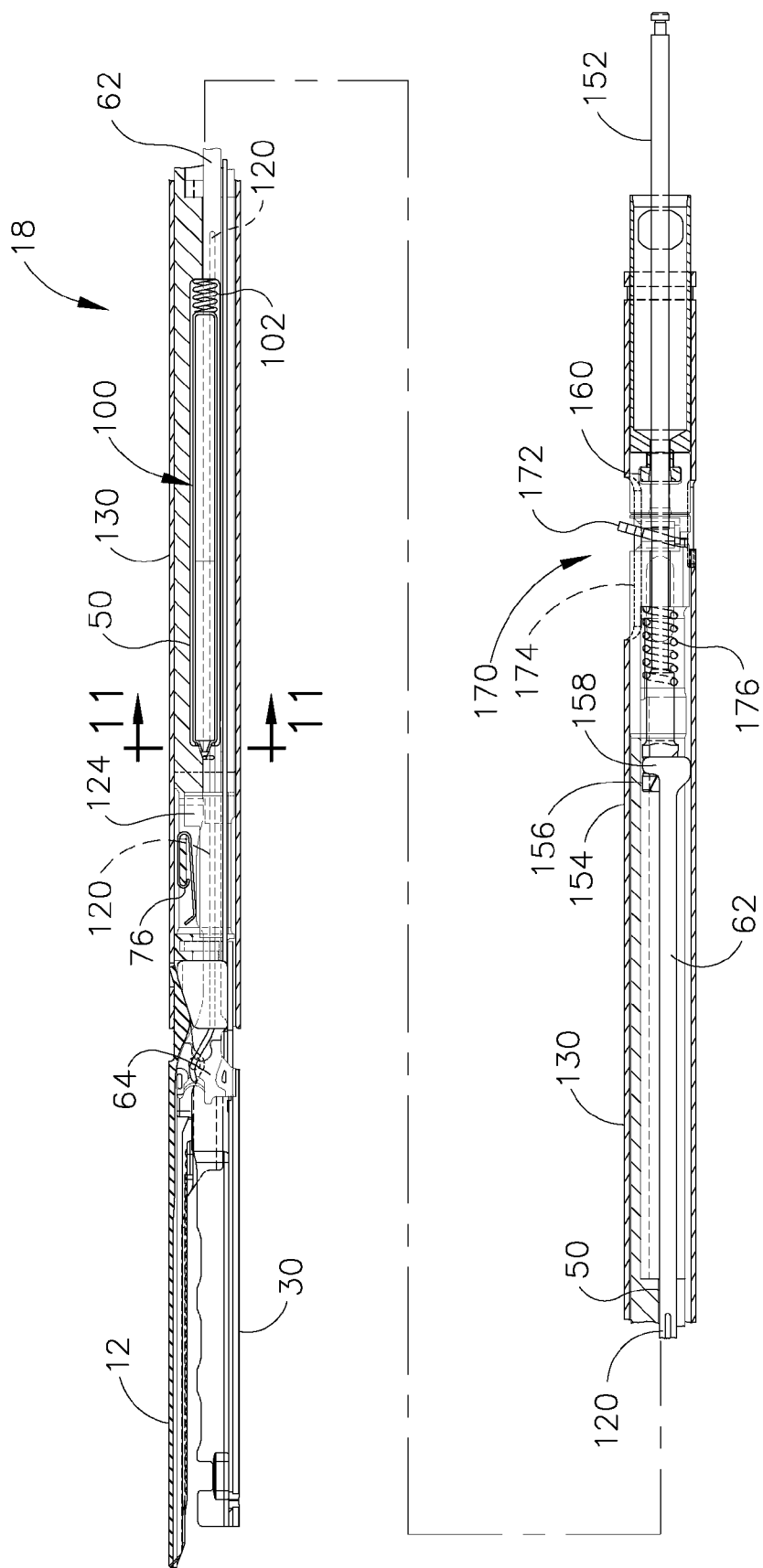
FIG. 3 is left side view in a elevation of the implement portion of the surgical stapling and severing instrument of FIG. 1 taken in cross section generally through a longitudinal axis and passing through an offset EAP syringe and receptacle that is in fluid communication with a dispensing groove in an E-beam firing bar.

With particular reference to FIG. 3, the handle 22 includes a firing trigger 150 (FIG. 1) that is drawn proximally toward the pistol grip 140 to cause a firing rod 152 to move distally in a proximal portion 154 of the elongate shaft 18. A distal bracket 156 of the firing rod 152 engages an upward proximal hook 158 of the firing bar 62. A dynamic seal 160 within the frame 50 seals to the firing rod 152 so that the implement portion 16 is pneumatically sealed when inserted into an insufflated abdomen.

An anti-backup mechanism 170 of the firing rod 152 may be advantageously included for a handle 22 that includes a multiple stroke firing trigger 150 and a retraction biased firing mechanism coupled to the firing rod 152 (not shown). In particular, an anti-backup locking plate 172 has the firing rod 152 pass through a closely fitting through hole (not shown) that binds when a retracting firing rod 152 tips the lock plate 172 backward as shown with the bottom of the locking plate 172 held in position within the frame 50. An anti-backup cam sleeve 174 is positioned distal to the anti-backup locking plate 172 and urged into contact by a more distal compression spring 176 through which the firing rod 152 passes and that is compressed within the frame 50. It should be appreciated that mechanisms in the handle 22 may manually release the anti-backup mechanism 170 for retraction of the firing rod 152.

In FIGS. 4-5, the end effector 14, which in the illustrative version is a staple applying assembly 20, is opened by having fluid bladder 24 deflated, drawing down lever tray 40 of the anvil 12, which pivots about pin 32 raising distal clamping section 41 thereby allowing positioning body tissue 180 between the anvil 12 and staple cartridge 42. The E-beam 64 has an upper pin 182 that resides within an anvil pocket 184 allowing repeated opening and closing of the anvil 12. An anvil slot 186 formed along the length of the anvil 12 receives the upper pin 182 when the anvil 12 is closed and the two piece firing bar 60 is distally advanced. A middle pin 188 slides within the staple cartridge 42 above the staple channel 30 in opposition to a bottom pin or foot 190 that slides along a bottom surface of the staple channel 30.

In FIGS. 6-7, the staple applying assembly 20 has been closed by expanding the fluid bladder (lift bag) 24, raising the lever tray 40 of the anvil 12 until flush with the outer sheath 130, with a proximal upwardly bent tip 192 of the lever tray 40 allowed to enter the top distal opening 131. This bent tip 192 in combination with the opening 131, advantageously allows greater radial travel for the anvil 12 as well as presenting an abutting surface rather than a piercing tip to the underlying fluid bladder 24. When the anvil 12 is closed, the upper pin 182 is aligned with the anvil slot 186 for firing and the tissue 180 is flattened to a thickness appropriate for severing and stapling.

Figure 11:
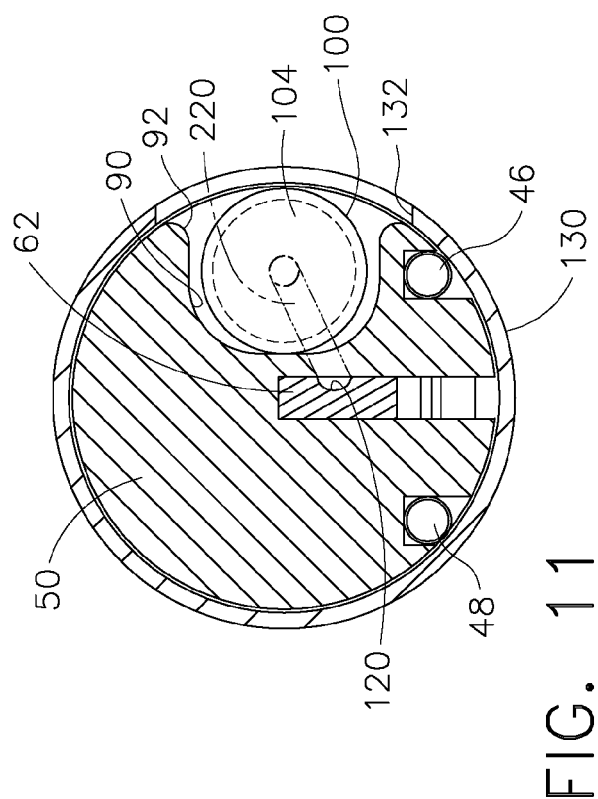
FIG. 11 is a front view in elevation of the elongate shaft of the surgical stapling and severing instrument of FIG. 3 taken along lines 11-11 taken through a distal end of the EAP medical substance syringe.
Figure 12:
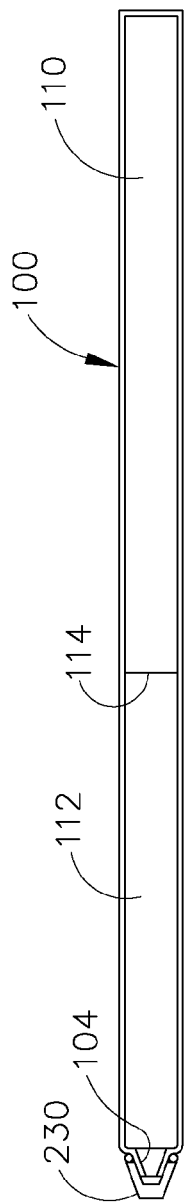
FIG. 12 is a left side view of the EAP medical substance syringe of FIG. 11.
Figure 13:
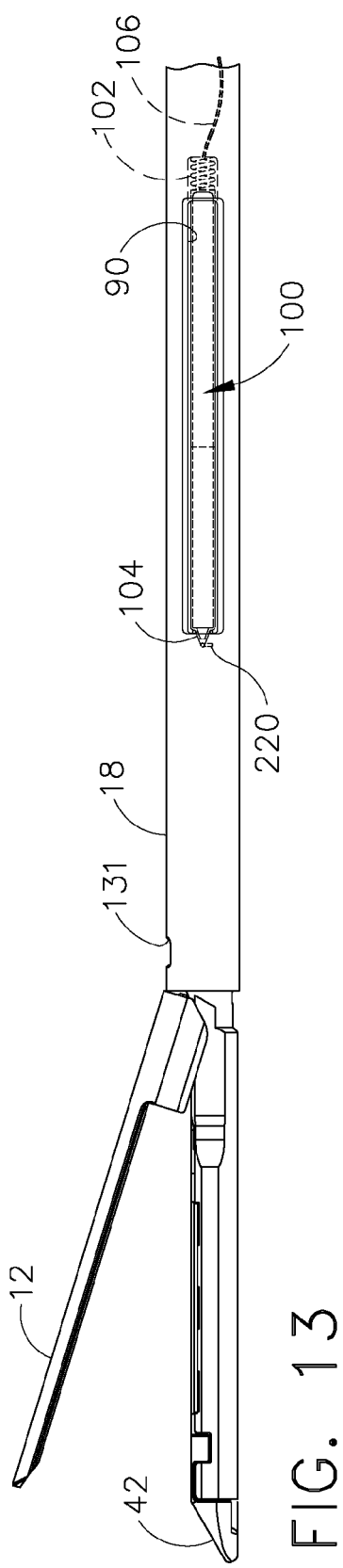
FIG. 13 is a left side view of the implement portion of the surgical stapling and severing instrument of FIG. 1 partially cut away to show proximal mountings for the EAP medical substance syringe.
Figure 14:
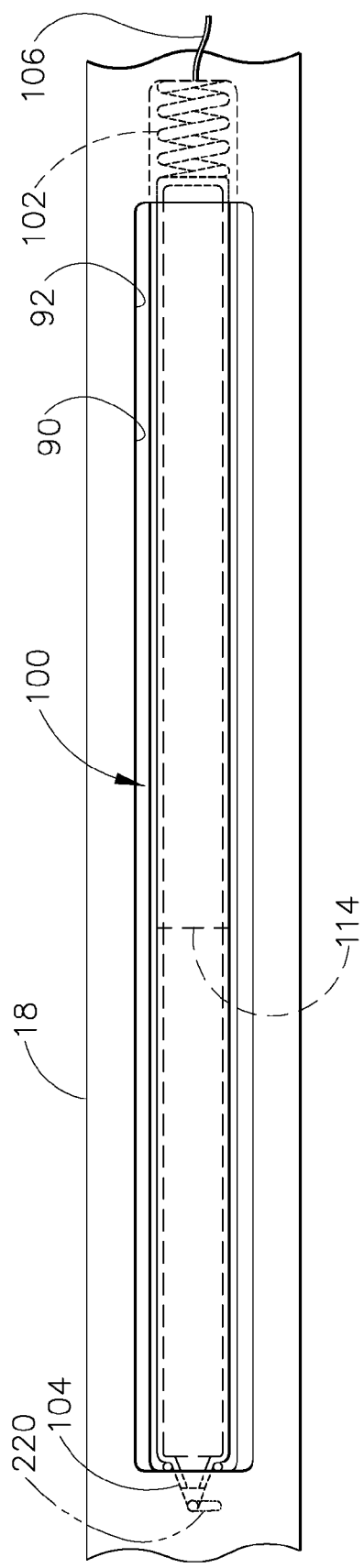
FIG. 14 is a left side detail view of the EAP medical substance syringe and receptacle of the elongate shaft of the surgical stapling and severing instrument of FIG. 13.

In FIGS. 7-8, the E-beam 64 is cut away to show its bottom foot 190 riding along a downwardly open laterally widened recess 200 that communicates with a narrow longitudinal slot 202 through which a vertical portion 204 of the E-beam 64 passes. A proximal aperture 206 to the narrow longitudinal slot 202 allows an assembly entrance for the lower foot 190. A bottom bump 208 is positioned on the firing bar 62 to drop into the proximal aperture 206 during an initial portion of firing travel under the urging of the clip spring 76 (FIG. 6) against the raised portion 80 of the firing bar 62 for proper engagement and for possible interaction with an end effector firing lockout mechanism (not shown). Also, this position allows for the end effector 14 to be pinched shut to facilitate insertion through a surgical entry point such as a cannula of a trocar (not shown). With reference to FIGS. 8-10, the firing bar guide 124 laterally contacts a portion of the firing bar 62 to close the corresponding portion of the lateral fluid groove 120. In FIG. 11, the EAP syringe 100 in the cylindrical cavity 90 has its distal dispensing cone 104 communicating with a radial fluid passage 220 formed in the frame 50 that communicates in turn with the lateral fluid groove 120. In FIG. 12, before installation in the surgical stapling and severing instrument 10, the EAP syringe 100 may be advantageously sealed with a disposable cap 230. In FIGS. 13-14, the EAP syringe 100 is shown without the disposable cap 230 and urged by spring 102 distally to engage the distal dispensing cone 104 into communication with the radial fluid passage 220.

It should be appreciated that one or more sensor in the surgical stapling and severing instrument 10 may sense a firing condition (e.g., movement of firing bar or mechanism coupled to the firing bar, position of the firing trigger, a separate user control to dispense, etc.) and activate dispensing control circuitry to effect dispensing.

In FIGS. 15-18, an alternate two-piece firing bar 300 is formed from longitudinally laminated left half and right half firing bar portions 302, 304 that form a firing bar 305 and attached to an E-beam 309. Thereby, fluid transfer down the firing bar 300 may be further constrained. In particular, a left side fluid groove 310 in the left half firing bar portion 302 transitions distally to a pair of aligned internal fluid grooves 312, 314 respectively in the left and right half firing bar portions 302, 304, defining an internal fluid passage 316. Since the E-beam 309 is laterally thicker and of short longitudinal length, a drilled fluid passage 320 is formed therein between a cutting surface 322 and an aft edge aligned to communicate with the internal fluid passage 316.

While the present embodiment has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, while a non-articulating shaft is described herein for clarity, it should be appreciated that medical substance dispensing may be incorporated into an articulating shaft. In addition, fluid conduits may be incorporated that pass through an articulation joint of a shaft to fluid bladder actuators that close an end effector.

As another example, while both medical substance dispensing and fluid actuated anvil closing are illustrated herein, applications consistent with aspects of various embodiments may include either of these features. Further, for applications in which an adhesive and/or cauterizing medical substance is dispensed, it should be appreciated that features such as staples may be omitted.

As another example, while a staple applying assembly 20 is illustrated herein, it should be appreciated that other end effectors (graspers, cutting devices, etc.) may benefit from either or both of fluid controlled closing and medical substance dispensing.

As yet another example, a receptacle for the EAP syringe may be formed in the handle rather than in the elongate shaft.

As yet an additional example, a symmetric arrangement for a second EAP syringe may be formed in the elongate channel so that two medical substances may be simultaneously dispensed during firing.

As yet a further example, while a staple applying apparatus provides an illustrative embodiment, it should be appreciated that other endoscopic instruments may benefit from the ability to dispense a liquid at or near a distal end thereof. Examples of instruments that may benefit include, but are not limited to, an ablation device, a grasper, a cauterizing tool, an anastomotic ring introduction device, a surgical stapler, a linear stapler, etc. As such, those instruments that do not employ a firing bar that serves herein as a convenient fluid passage to a cutting surface may instead incorporate ducting or fluid conduits to an appropriate location.

While an electroactive polymer plunger has various advantages, it should be appreciated that other types of actuated devices may be employed to dispense a medical substance to the end effector.

Figure 19:
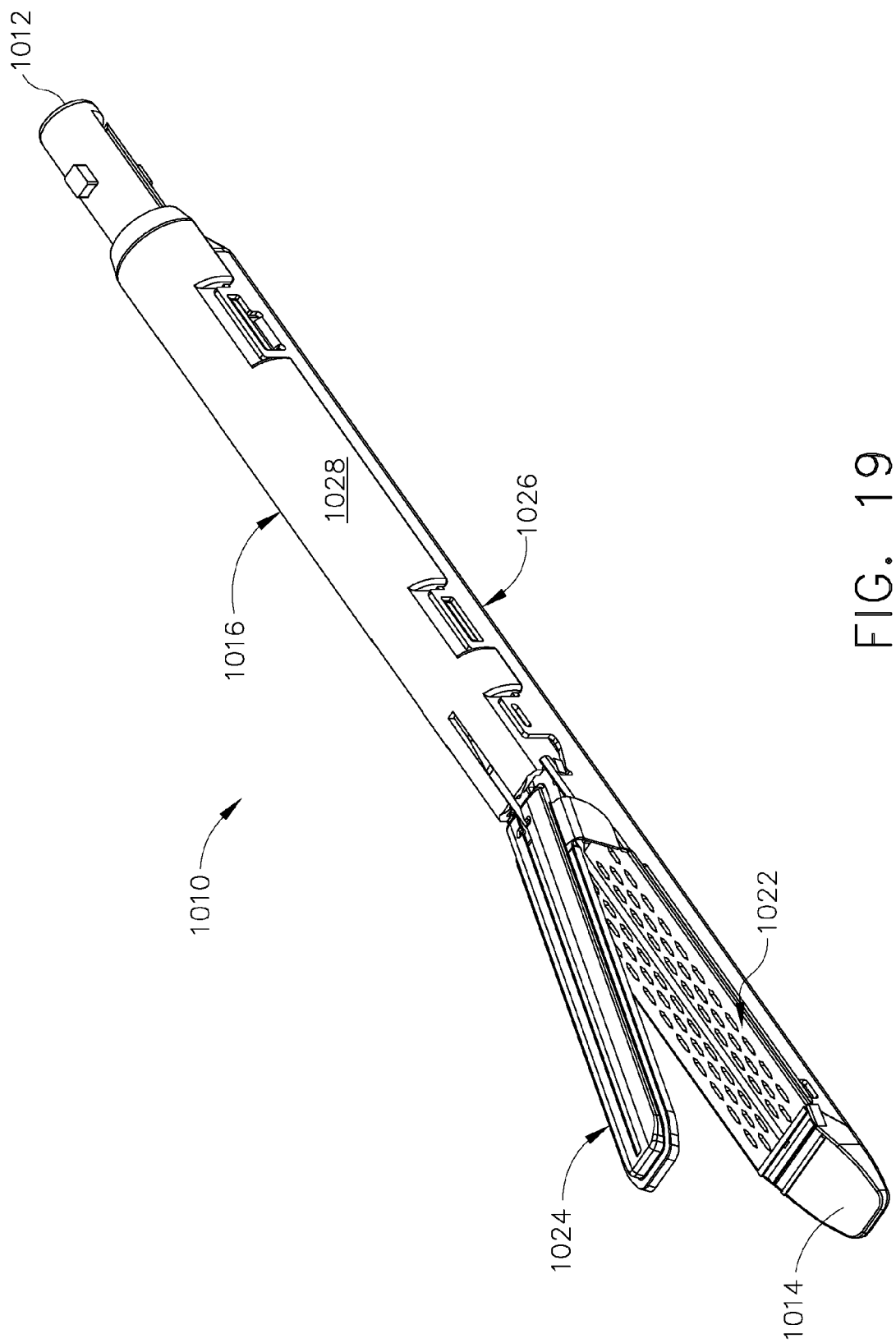
FIGS. 19-20 illustrate various embodiments of a disposable loading unit.
Figure 20:
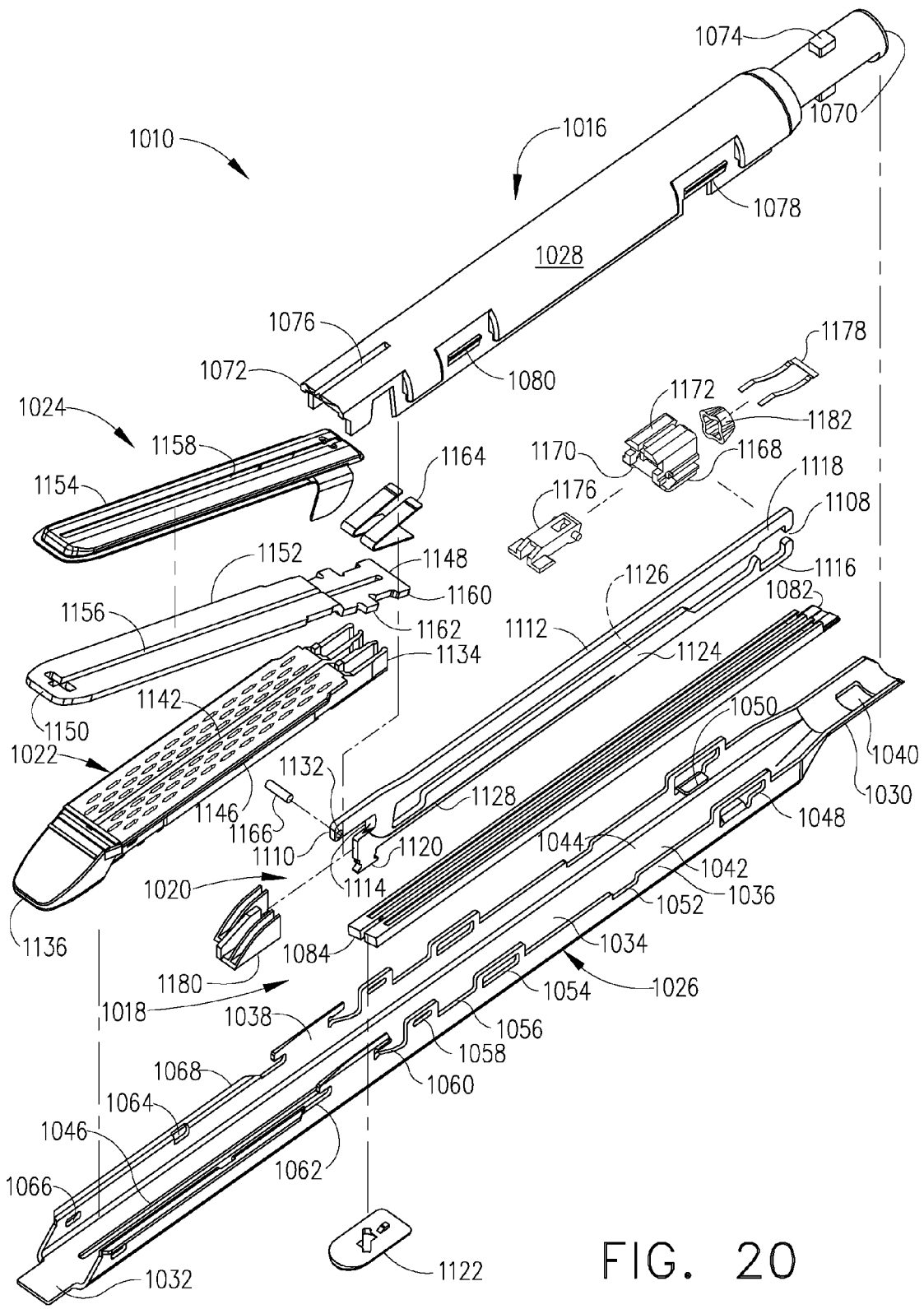

For example, FIGS. 19-20 illustrate various embodiments of a disposable loading unit 1010, with FIG. 20 showing an exploded view of the disposable loading unit 1010. The disposable loading unit 1010 includes a first end 1012 configured for releasable connection to a surgical instrument (see FIG. 33), and a second end 1014 opposite the first end 1012. The disposable loading unit 1010 comprises a housing assembly 1016, an agent cartridge 1018, a knife assembly 1020, a staple cartridge 1022, and an anvil assembly 1024. The disposable loading unit 1010 may be removed and discarded after a single use.

The housing assembly 1016 comprises a channel 1026 and a channel cover 1028 connected to the channel 1026. The channel 1026 and the channel cover 1028 may be fabricated from any suitable material such as, for example, a plastic. The channel 1026 includes a first end 1030 proximate the first end 1012 of the disposable loading unit 1010 and a second end 1032 proximate the second end 1014 of the disposable loading unit 1010. The channel 1026 comprises a base 1034, a first wall 1036, and a second wall 1038. According to various embodiments, the base 1034 defines an opening 1040 proximate the first end 1030 of the channel 1026, a first slot 1042 proximate the first end 1030 of the channel 1026, a second slot 1044 proximate the first end 1030 of the channel 1026, and a third slot 1046 proximate the second end 1032 of the channel. The first wall 1036 is connected to the base 1034 and extends generally perpendicular therefrom. The second wall 1038 is connected to the base 1034, extends generally perpendicular therefrom, and is opposite the first wall 1036. The second wall 1038 may be a minor-image of the first wall 1036, and the first and second walls 1036, 1038 may be fabricated integral with the base 1034. According to various embodiments, each of the first and second walls 1036, 1038 define a fourth slot 1048, a first tab 1050, a first indent 1052, a fifth slot 1054, a second indent 1056, a sixth slot 1058, a third indent 1060, a fourth indent 1062, a seventh slot 1064, an eighth slot 1066, and a first flange 1068.

The channel cover 1028 includes a first end 1070 proximate the first end 1012 of the disposable loading unit 1010 and a second end 1072 opposite the first end 1070, and may be symmetric along an axis that extends from the first end 1070 of the channel cover 1028 to the second end 1072 of the channel cover 1028. The channel cover 1028 is configured to engage with the channel 1026 at a plurality of locations. According to various embodiments, the channel cover 1028 defines a pair of coupling pegs 1074 proximate the first end 1070 of the channel cover 1028 that extends from the channel cover 1028. One of the coupling pegs 1074 passes through the opening 1040 defined by the channel 1026. The channel cover 1028 also defines a slit 1076 proximate the second end 1072 of the channel cover 1028. According to various embodiments, the channel cover 1028 defines a first pair of tabs 1078 that pass through and engage with the fourth slots 1048, a first pair of interior projections that mate with the first indents 1052, a second pair of tabs 1080 that pass through and engage with the fifth slots 1054, a second pair of interior projections that mate with the second indents 1056, and a third pair of interior projections that engage with the sixth slots 1058. According to other embodiments, the channel 1026 and the channel cover 1028 may be fabricated to include other arrangements of tabs, slots, projections, indents, etc. that may be utilized to connect the channel cover 1028 to the channel 1026.

The agent cartridge 1018 is connected to the housing assembly 1016 and houses at least one medical agent. The medical agent may be any type of medical agent. For example, the medical agent may comprise an anesthetic, an adhesive, an antibiotic, a cauterizing substance, a coagulant, a growth hormone, a hemostatic agent, a sealant, etc., or any combination thereof.

Figure 21:
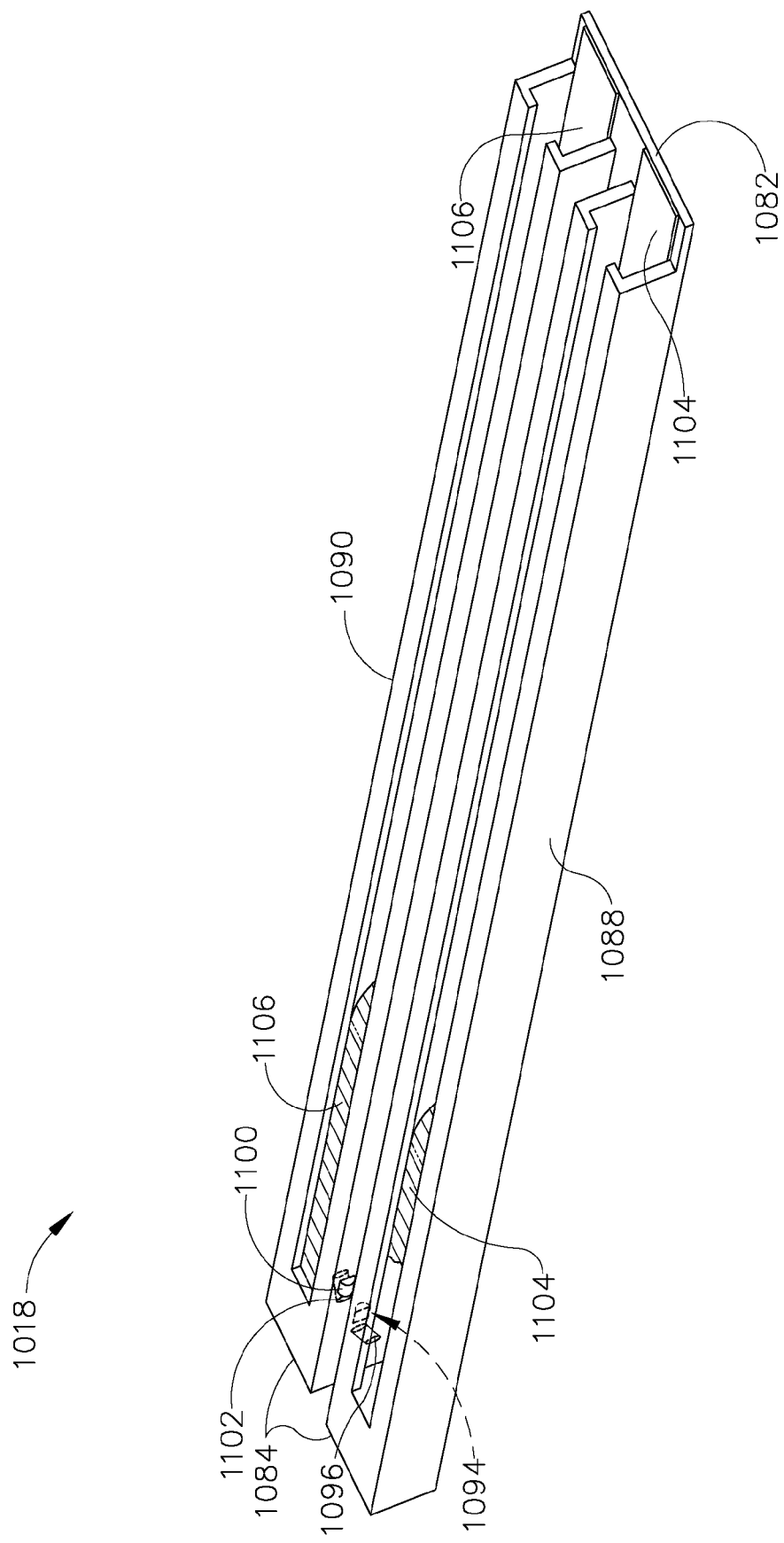
FIG. 21 illustrates various embodiments of an agent cartridge.

The agent cartridge 1018 includes a first end 1082 proximate the first end 1012 of the disposable loading unit 1010 and a second end 1084 opposite the first end 1082. The agent cartridge 1018 comprises a body 1086 (see FIG. 24) that may be fabricated from any suitable material (e.g., a plastic) that is compatible with the medical agent. According to various embodiments, the body 1086 comprises a first section 1088 and a second section 1090. The first section 1088 may define a first spline that extends therefrom, and passes through and engages with the first slot 1042 of the base 1034 of the channel 1026. As shown in FIG. 21, the first section 1088 may also define a first projection 1094 and a first dispensing port 1096 proximate the second end 1084 of the agent cartridge 1018. The first projection 1094 may be of any shape (e.g., rectangular, triangular, hemispherical, etc.). The first dispensing port 1096 is positioned between the first projection 1094 and the second end 1084 of the agent cartridge 1018. The second section 1090 is spaced apart from the first section 1088 and may be a mirror-image thereof. The second section 1090 may define a second spline that extends therefrom, and passes through and engages with the second slot 1044 of the base 1034 of the channel 1026. As shown in FIG. 21, the second section 1090 may define a second projection 1100 and a second dispensing port 1102 proximate the second end 1084 of the agent cartridge 1018. The second projection 1100 may be of any shape (e.g., rectangular, triangular, hemispherical, etc.). The second dispensing port 1102 is positioned between the second projection 1100 and the second end 1084 of the agent cartridge 1018. According to other embodiments, the body 1086 may be fabricated to include other arrangements of splines, tabs, fasteners, etc. that may be utilized to connect the agent cartridge 1018 to the housing assembly 1016.

According to various embodiments, the agent cartridge 1018 also comprises a first sealing member 1104 (see FIG. 21) and a second sealing member 1106 (see FIG. 21). The first sealing member 1104 is connected to the first section 1088 and cooperates with the first section 1088 to house a medical agent. Similarly, the second sealing member 1106 is connected to the second section 1090 and cooperates with the second section 1090 to house a second medical agent. The first medical agent may be the same or different than the second medical agent.

The knife assembly 1020 is connected to the housing assembly 1016, and includes a first end 1108 proximate the first end 1012 of the disposable loading unit 1010 and a second end 1110 opposite the first end 1108. The knife assembly 1020 comprises a body 1112 and a cutting surface 1114. According to various embodiments, the cutting surface 1114 comprises a portion of a knife blade that is connected to the body 1112 proximate the second end 1110 of the knife assembly 1020. The body 1112 may be fabricated from any suitable material such as, for example, a plastic. According to various embodiments, the body 1112 comprises a first clamping member 1116 proximate the first end 1108 of the knife assembly 1020, a second clamping member 1118 proximate the first end 1108 of the knife assembly 1020, and a foot member 1120 proximate the second end 1110 of the knife assembly 1020. The foot member 1120 passes through the third slot 1046 of the base 1034 of the channel 1026 and is mated with a retainer 1122 that is external to the housing assembly 1016 and serves to slidably connect the body 1112 to the housing assembly 1016 such that the knife assembly 1020 can be selectively advanced along the third slot 1046 toward the second end 1032 of the channel 1026.

The body 1112 of the knife assembly 1020 also comprises a first surface 1124 and a second surface 1126 (see FIG. 24) that is opposite the first surface 1124. The first surface 1124 of the body 1112 is adjacent the first section 1088 of the agent cartridge 1018, and the second surface 1126 of the body 1112 is adjacent the second section 1090 of the agent cartridge 1018. The first surface 1124 of the body 1112 defines a first groove 1128 and the second surface 1126 of the body 1112 defines a second groove 1130 (see FIG. 24). The first groove 1128 is proximate the cutting surface 1114 of the knife assembly 1020 and may extend any distance along the first surface 1124 of the body 1112 toward the first end 1108 of the knife assembly 1020. The first groove 1128 is adjacent the first dispensing port 1096 and is configured to receive the first projection 1094 of the first section 1088 of the body 1086. The second groove 1130 is proximate the cutting surface 1114 of the knife assembly 1020 and may extend any distance along the second surface 1126 of the body 1112 toward the first end 1108 of the knife assembly 1020. The second groove 1130 is adjacent the second dispensing port 1102 and is configured to receive the second projection 1100 of the second section 1090 of the body 1086. Each of the first and second grooves 1128, 1130 may be of any shape (e.g., rectangular, triangular, hemispherical, etc.) suitable for respectively receiving the first projection 1094 and the second projection 1100. The body 1112 of the knife assembly 1020 may also define an opening 1132 that extends from the first surface 1124 to the second surface 1126 proximate the second end 1110 of the knife assembly 1020.

The staple cartridge 1022 is connected to the housing assembly 1016. The staple cartridge 1022 includes a first end 1134 and a second end 1136 opposite the first end 1134. The second end 1136 of the staple cartridge 1022 is proximate the second end 1014 of the disposable loading unit 1010. The staple cartridge 1022 may be similar to other staple cartridges known in the art. For example, the staple cartridge 1022 may comprise a plurality of surgical fasteners and a plurality of corresponding pushers. According to various embodiments, the staple cartridge 1022 defines a slot 1142 that is aligned with the third slot 1046 of the base 1034 of the channel 1026 and extends from the first end 1134 of the staple cartridge 1022 toward the second end 1136 of the staple cartridge 1022. The staple cartridge 1022 may also define tabs that extend from the staple cartridge 1022 and pass through and engage with the seventh slots 1064 and the eighth slots 1066 of the channel 1026, and may further comprise flanges 1146 which frictionally engage the first and second walls 1036, 1038 of the channel 1026 proximate the second end 1032 of the channel 1026. According to other embodiments, the staple cartridge 1022 may be fabricated to include other arrangements of tabs, flanges, fasteners, etc. that may be utilized to connect the staple cartridge 1022 to the housing assembly 1016.

The anvil assembly 1024 is connected to the housing assembly 1016. The anvil assembly 1024 includes a first end 1148 and a second end 1150 opposite the first end 1148. The second end 1150 of the anvil assembly 1024 is proximate the second end 1014 of the disposable loading unit 1010. The anvil assembly 1024 may be similar to other anvil assemblies known in the art. For example, the anvil assembly 1024 is moveable between an open position and a closed position, and may comprise an anvil plate 1152 and an anvil body 1154 connected to the anvil plate 1152. According to various embodiments, the anvil plate 1152 defines a slot 1156 that is aligned with the slot 1142 of the staple cartridge 1022, and the anvil body 1154 defines a slot 1158 that is aligned with the slot 1156 of the anvil plate 1152. The anvil plate 1152 may also define a first pair of ears 1160 proximate the first end 1148 of the anvil assembly 1024 and a second pair of ears 1162 positioned between the first pair of ears 1160 and the second end 1150 of the anvil assembly 1024. One of the ears of the second pair of ears 1162 is engaged with the third indent 1060 defined by the first wall 1036 of the channel 1026, and the other ear of the second pair of ears 1162 is engaged with the third indent 1060 defined by the second wall 1038 of the channel 1026. A spring member 1164 or other biasing arrangement may be utilized to urge the anvil assembly 1024 to the open position, and an anvil pin 1166 that passes through the opening 1132 of the knife assembly 1020 may be utilized to urge the anvil assembly 1024 toward the closed position. According to other embodiments, the anvil assembly 1024 may be fabricated to include other fastener arrangements that may be utilized to connect the anvil assembly 1024 to the housing assembly 1016.

The disposable loading unit 1010 may further comprise a first medical agent driver 1168 proximate the first end 1082 of the agent cartridge 1018 and a second medical agent driver 1170 (see FIG. 24) proximate the first end 1082 of the agent cartridge 1018. According to various embodiments, the first and second medical agent drivers 1168, 1170 may comprise a portion of a drive block 1172 that is coupled to the knife assembly 1020 at the first end 1108 thereof. For such embodiments, the first medical agent driver 1168 may be configured to slidably fit within the first section 1088 of the body 1086 of the agent cartridge 1018, and the second medical agent driver 1170 may be configured to slidably fit within the second section 1090 of the body 1086 of the agent cartridge 1018. According to other embodiments, the first medical agent driver 1168 may comprise an electrically activated polymer that is in contact with the first section 1088 of the body 1086 of the agent cartridge 1018 as shown in FIGS. 13 and 14. Similarly, the second medical agent driver 1170 may comprise an electrically activated polymer that is in contact with the second section 1090 of the body 1086 of the agent cartridge 1018. For such embodiments, each of the first and second medical agent drivers 1168, 1170 may be electrically connected to a contact 1174 (see FIG. 32) that is proximate the first end 1012 of the disposable loading unit 1010 and is connected to a voltage source.

As shown in FIG. 2, the disposable loading unit 1010 may also comprise a lock member 1176 connected to the drive block 1172, a retainer 1178 for coupling the lock member 1176 to the drive block 1172, and a sled 1180 positioned proximate the second end 1110 of the knife assembly 1020. The drive block 1172, the lock member 1176, the retainer 1178 and the sled 1180 may be similar to those known in the art. The disposable loading unit 1010 may further comprise a firing member adapter 1182 connected to the drive block 172. The firing member adapter 1182 is configured for receiving a firing member that does not comprise a portion of the disposable loading unit 1010.

FIG. 22 illustrates various embodiments of the disposable loading unit 1010. For purposes of clarity only, certain portions of the disposable loading unit 1010 are not shown in this figure. The first and second clamping members 1116, 1118 are connected to the drive block 1172, and the lock member 1176 and the retainer 1178 are also connected to the drive block 1172. The first medical agent driver 1168 is connected to the drive block 1172, and the sled 1180 is proximate the second end 1110 of the knife assembly 1020. The general positions of the shown components relative to the channel 1026 represent the positions of the components prior to the advancement of the firing member (i.e., the pre-fire positions).

FIG. 23 illustrates various embodiments of the disposable loading unit 1010. For purposes of clarity only, certain portions of the disposable loading unit 1010 are not shown in this figure. FIG. 23 is similar to FIG. 22, and shows that the first medical agent driver 1168 is aligned with the first section 1088 of the body 1086 of the agent cartridge 1018. The general positions of the shown components relative to the channel 1026 represent the positions of the components prior to the advancement of the firing member (i.e., the pre-fire positions).

Figure 24:
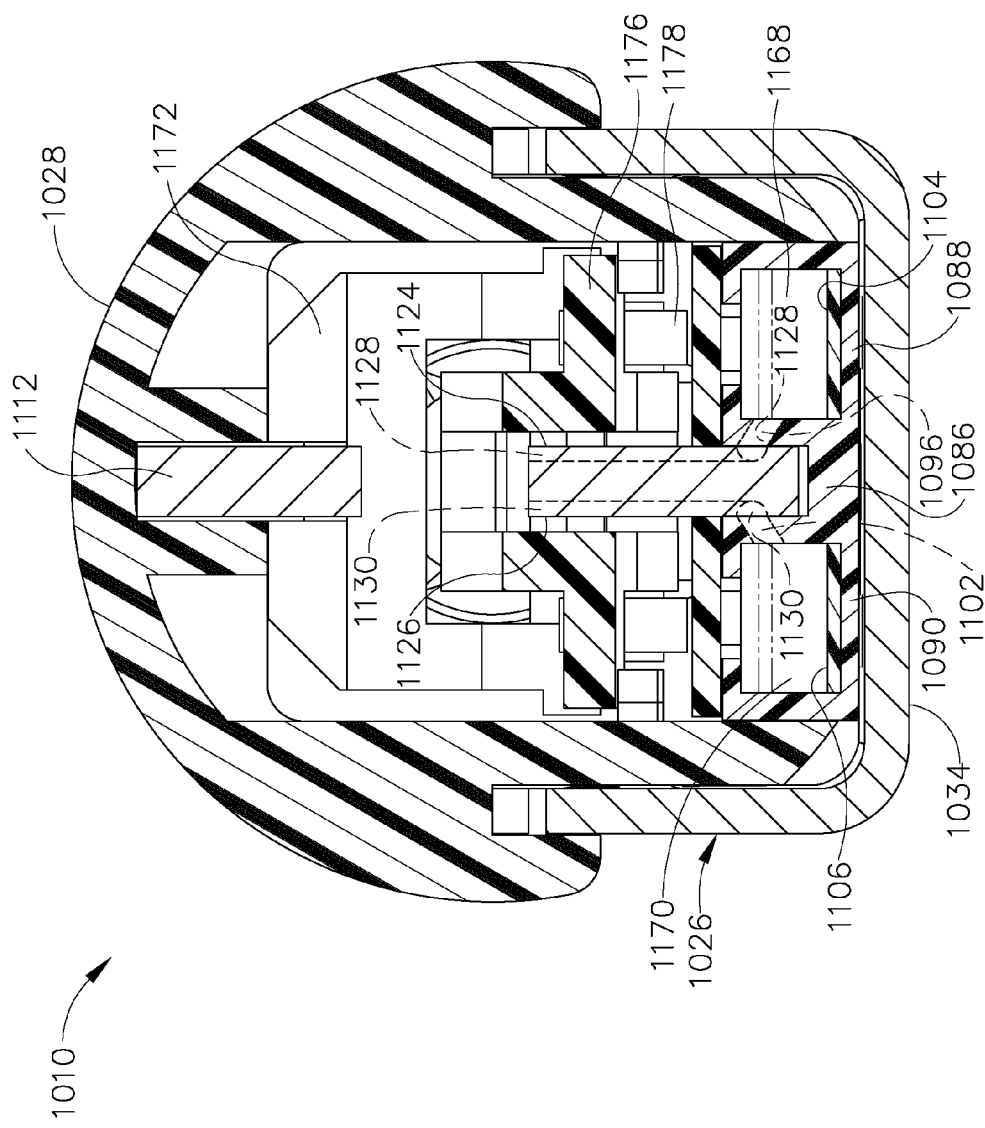
FIG. 24 illustrates various embodiments of a disposable loading unit.

FIG. 24 illustrates various embodiments of the disposable loading unit 1010, and shows a cross-section of the disposable loading unit 1010 along line 6-6 of FIG. 23. As shown in FIG. 24, the first and second dispensing ports 1096, 1102 may pass through the respective first and second sections 1088, 1090 at an angle relative to the base 1034 of the channel 1026.

FIG. 25 illustrates various embodiments of the disposable loading unit 1010. For purposes of clarity only, certain portions of the disposable loading unit 1010 are not shown in this figure. The anvil assembly 1024 is shown in the open position relative to the staple cartridge 1022 in FIG. 25. The general positions of the shown components relative to the channel 1026 represent the positions of the components prior to the advancement of the firing member (i.e., the pre-fire positions).

FIG. 26 illustrates various embodiments of the disposable loading unit 1010. For purposes of clarity only, certain portions of the disposable loading unit 1010 are not shown in this figure. FIG. 26 is similar to FIG. 25, but also shows the first section 1088 of the body 1086 of the agent cartridge 1018.

FIG. 27 illustrates various embodiments of the disposable loading unit 1010, and is an enlarged version of a portion of the disposable loading unit 1010 illustrated in FIG. 26.

FIG. 28 illustrates various embodiments of the disposable loading unit 1010, and is an enlarged version of a portion of the disposable loading unit 1010 illustrated in FIG. 26.

FIG. 29 illustrates various embodiments of the disposable loading unit 1010. For purposes of clarity only, certain portions of the disposable loading unit 1010 are not shown in this figure. The general positions of the shown components relative to the channel 1026 represent the positions of the components after the advancement of the firing member (i.e., the post-fire positions). As shown in FIG. 29, the anvil assembly 1024 is in the closed position, and the post-fire positions of the knife assembly 1020, the anvil assembly 1024, the first medical agent driver 1168, the drive block 1172, and the lock member 1176 are different than their pre-fire positions relative to the channel 1026.

FIG. 30 illustrates various embodiments of the disposable loading unit 1010, and is an enlarged version of a portion of the disposable loading unit 1010 illustrated in FIG. 29. As shown in FIG. 30, the post-fire position of the first medical agent driver 1168 may be some distance from the first dispensing port 1096. Similarly, the post-fire position of the second medical agent driver 1170 may be some distance from the second dispensing port 1102.

FIG. 31 illustrates various embodiments of the disposable loading unit 1010. For purposes of clarity only, certain portions of the disposable loading unit 1010 are not shown in this figure. FIG. 31 is similar to FIG. 22, but shows the first section 1088 of the body 1086 of the agent cartridge 1018, and also shows the first medical agent driver 1168 embodied as an electrically activated polymer. FIG. 31 also illustrates the conductors 1184 that electrically connect the first medical agent driver 1168 and the contact 1174. The general positions of the shown components relative to the channel 1026 represent the positions of the components prior to the advancement of the firing member (i.e., the pre-fire positions).

FIG. 32 illustrates various embodiments of the disposable loading unit 1010. For purposes of clarity only, certain portions of the disposable loading unit 1010 are not shown in this figure. FIG. 32 is similar to FIG. 26, but shows the first medical agent driver 1168 embodied as an electrically activated polymer. FIG. 32 also illustrates the contact 1174 and the conductors 1184 that electrically connect the contact 1174 and the first medical agent driver 1168. The general positions of the shown components relative to the channel 1026 represent the positions of the components prior to the advancement of the firing member (i.e., the pre-fire positions).

Figure 33:
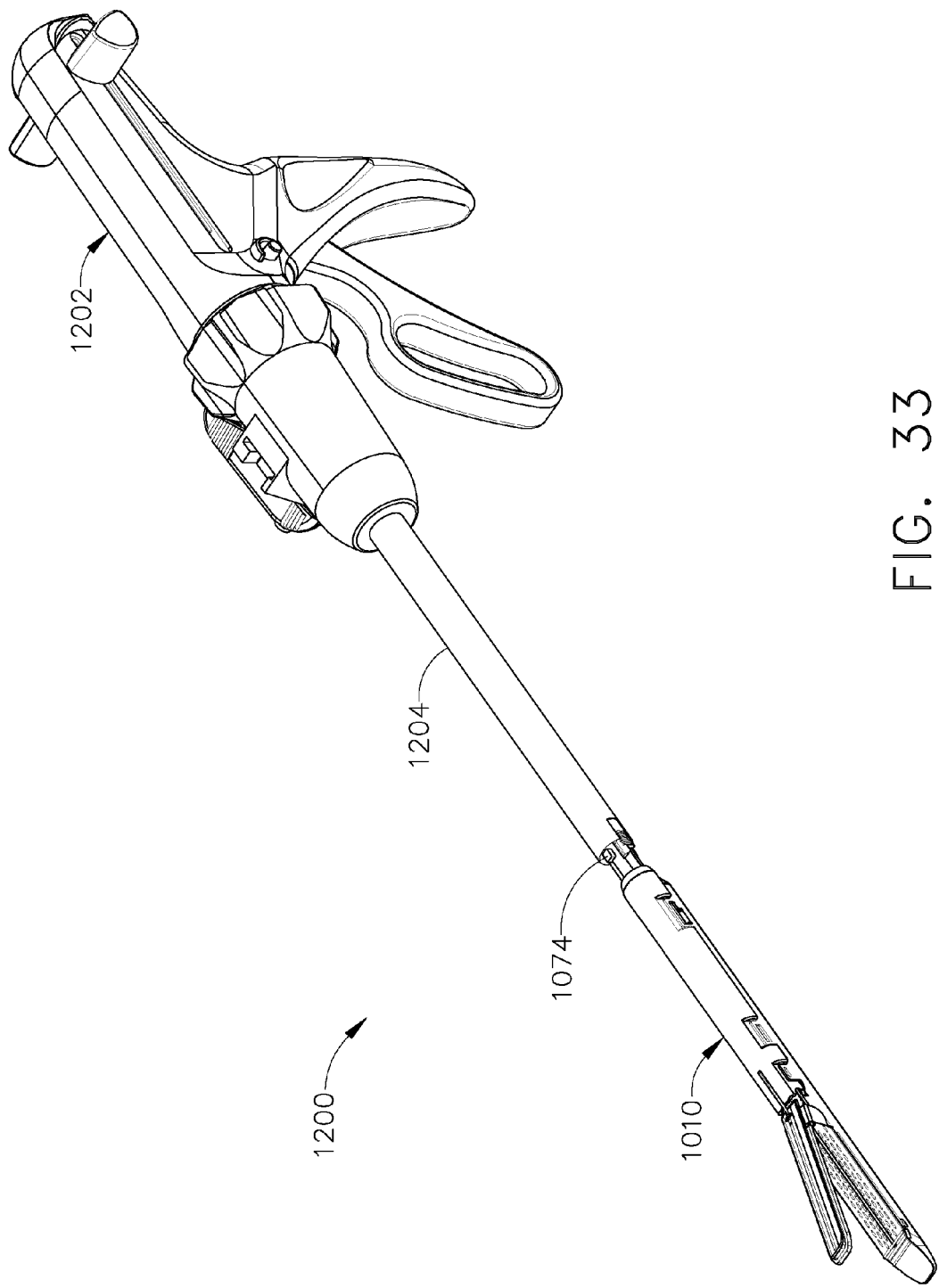
FIG. 33 illustrates various embodiments of a surgical instrument.

FIG. 33 illustrates various embodiments of a surgical instrument 1200. The surgical instrument 1200 includes a handle assembly 1202, an elongated body 1204 connected to the handle assembly 1202, and a disposable loading unit 1010 releasably connected to the elongated body 1204. The disposable loading unit 1010 may be releasably connected to the elongated body 1204 in any manner. For example, the disposable loading unit 1010 may be releasably connected to the elongated body 1204 via the coupling pegs 1074 described hereinabove. The handle assembly 1202 and the elongated body 1204 may be similar to other handle assemblies and elongated bodies known in the art. For example, the handle assembly 1202 may include means for advancing a firing member that is surrounded by the elongated body 1204 and is utilized to advance the drive block 1172 of the disposable loading unit 1010.

In operation, when the firing member is advanced, the advancement of the firing member causes the drive block 1172 to advance toward the second end 1014 of the disposable loading unit 1010. As the drive block 1172 advances, the knife assembly 1020 advances toward the second end 1014 of the disposable loading unit 1010. The advancement of the knife assembly 1020 causes the anvil pin 1166 to cooperate with the anvil body 1154 to urge the anvil assembly 1024 toward the closed position. The advancement of the knife assembly 1020 also causes the sled 1180 to advance toward the second end 1014 of the disposable loading unit 1010. As the sled 1180 advances, the angled leading edges of the sled 1180 sequentially contact pushers supported within the staple cartridge 1022, causing the pushers to urge surgical fasteners from the staple cartridge 1022 in a known manner.

For embodiments where the first and second medical agent drivers 1168, 1170 are coupled to the knife assembly 1020, the advancement of the drive block 1172 advances the first and second medical agent drivers 1168, 1170 within the first and second sections 1088, 1090 of the body 1086 toward the second end 1084 of the agent cartridge 1018. As the first and second medical agent drivers 1168, 1170 advance, they make contact with the first and second sealing members 1104, 1106 and urge the first and second medical agents out of the first and second dispensing ports 1096, 1102. Because the post-fire positions of the first and second medical agent drivers 1168, 1170 may be some distance from the first and second dispensing ports 1096, 1102, some medical agent may still remain housed by the agent cartridge 1018 after the first and second medical agent drivers 1168, 1170 advance from their pre-fire positions to their post-fire positions.

For embodiments where the first and second medical agent drivers 1168, 1170 are electrically activated polymers, the advancement of the firing member causes an electrical connection to be made with the contact 1174, causing a voltage to be applied to the first and second medical agent drivers 1168, 1170. In response to the applied voltage, the first and second medical agent drivers 1168, 1170 expand within the first and second sections 1088, 1090 of the body 1086 of the agent cartridge 1018 and urge the first and second medical agents out of the first and second dispensing ports 1096, 1102.

With the first projection 1094 and the second projection 1100 serving as stops which restrict the flow of the first and second medical agents along the grooves 1128, 1130 in the direction toward the first end 1012 of the disposable loading unit 1010, the medical agents urged out of the first and second dispensing ports 1096, 1102 advance along the respective grooves 1128, 1130 toward the cutting surface 1114 of the disposable loading unit 1010. As the knife assembly 1020 advances along the slot 1142 defined by the staple cartridge 1022, the staple cartridge 1022 also serves to keep the medical agents in the grooves 1128, 1130 until the medical agents exit the grooves 1128, 1130 proximate the cutting surface 1114. The medical agents are thus effectively delivered to the site of the cutting and stapling.

After a single use, the disposable loading unit 1010 is removed from the elongated body 1204 and may be replaced with another disposable loading unit 1010 for another use. This process may be repeated any number of times. Therefore, the handle assembly 1202 and the elongated body 1204 connected thereto may be reused any number of times.

While several embodiments have been described, it should be apparent, however, that various modifications, alterations and adaptations to those embodiments may occur to persons skilled in the art with the attainment of some or all of the advantages of the various embodiments. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed embodiments as defined by the appended claims.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An assembly of a surgical instrument, comprising:
   a housing;
   a cutting member relatively movable with respect to the housing, wherein the cutting member comprises a cutting surface, a body including a first surface, and a groove at least partially defined by the first surface; and
   an agent cartridge connected to the housing, wherein the agent cartridge includes a cavity configured to house a medical agent therein, wherein the cutting member groove is in fluid communication with the cavity, and wherein said cutting member is configured to movably interact with said agent cartridge such that movement of said cutting member relative thereto in a first direction causes said medical agent housed within said cavity to be delivered through the groove and dispensed proximate to the cutting surface.

2. The assembly of claim 1, wherein the agent cartridge comprises a body, and wherein the agent cartridge body and the cutting member groove define a passage therebetween configured to deliver the medical agent from the cavity proximate to the cutting surface.

3. The assembly of claim 1, wherein the agent cartridge includes a dispensing port in fluid communication with the cavity, and wherein the groove is configured such that it remains in fluid communication with the dispensing port as the cutting member is moved relative to the housing.

4. The assembly of claim 1, wherein the surgical instrument comprises a handle and an elongate body extending from the handle, and wherein the housing is configured to be releasably connected to the elongate body.

5. The assembly of claim 1, wherein the housing is fixedly connected to a portion of the surgical instrument.

6. The assembly of claim 1, wherein the agent cartridge is directly connected to the housing.

7. The assembly of claim 1, further comprising a staple cartridge connected to the housing.

8. The assembly of claim 1, further comprising a medical agent driver extending from the cutting member, wherein the driver is configured to engage the agent cartridge and dispense the medical agent from the agent cartridge cavity to the groove as the cutting member is moved relative to the housing.

9. An assembly of a surgical instrument, comprising:
   a housing;
   a member relatively movable with respect to the housing, wherein the member comprises a cutting surface, a body including a first surface, and a passage at least partially defined by the first surface; and
   an agent cartridge, wherein the agent cartridge includes a medical agent storage portion configured to house a medical agent therein, wherein the member passage is in fluid communication with the medical agent storage portion, and wherein said movable member is configured to movably interact with said medical agent storage portion such that axial movement of said movable member relative thereto in a first direction causes said medical agent housed within said medical agent storage portion to be delivered through the passage to the cutting surface.

10. The assembly of claim 9, wherein the surgical instrument comprises a handle and an elongate body extending from the handle, and wherein the housing is configured to be releasably connected to the elongate body.

11. The assembly of claim 9, wherein the housing is fixedly connected to a portion of the surgical instrument.

12. The assembly of claim 9, wherein the agent cartridge includes a dispensing port in fluid communication with the medical agent storage portion, and wherein the passage is configured such that it remains in fluid communication with the dispensing port as the member is moved relative to the housing.

13. The assembly of claim 9, wherein the agent cartridge is directly connected to the housing.

14. The assembly of claim 9, further comprising a staple cartridge connected to the housing.

15. The assembly of claim 9, further comprising a medical agent driver extending from the movable member, wherein the driver is configured to engage the agent cartridge and dispense the medical agent from the medical agent storage portion to the passage as the cutting member is moved relative to the housing.

* * * * *